United States Patent [19]

Yang et al.

[11] Patent Number: 4,517,371

[45] Date of Patent: May 14, 1985

[54] PROCESS FOR THE SYNTHESIS OF CARBOXYLIC ANHYDRIDES USING A VANADIUM, PHOSPHORUS OXYGEN CONTAINING CATALYST COMPOSITION

[75] Inventors: Tai-Cheng Yang, Mahwah; Krishna K. Rao, Paterson; I-Der Huang, Upper Saddle River, all of N.J.

[73] Assignee: Exxon Research & Engineering Co., Florham Park, N.J.

[21] Appl. No.: 492,995

[22] Filed: May 9, 1983

Related U.S. Application Data

[60] Division of Ser. No. 326,543, Dec. 2, 1981, Pat. No. 4,392,986, which is a continuation-in-part of Ser. No. 309,725, Oct. 8, 1981, abandoned, which is a continuation of Ser. No. 202,262, Oct. 30, 1980, abandoned.

[51] Int. Cl.$^3$ .................. C07D 493/04; C07D 307/89; C07D 307/60
[52] U.S. Cl. .................. 549/239; 549/245; 549/248; 549/253; 549/257; 549/259; 549/260
[58] Field of Search .............. 549/259, 248, 245, 260, 549/239, 253, 257

[56] References Cited

U.S. PATENT DOCUMENTS 4,317,778 3/1982 Blum ................................ 549/260
4,333,853 6/1982 Milberger et al. ................ 549/259

*Primary Examiner*—John M. Ford
*Assistant Examiner*—Bernard I. Dentz
*Attorney, Agent, or Firm*—Robert A. Maggio

[57] ABSTRACT

A vanadium, phosphorus oxygen containing catalyst composition capable of partially oxidizing hydrocarbons (e.g., n-butane) to form a carboxylic anhydride (e.g., maleic anhydride), a process for preparing this catalyst, and a process for using this catalyst to form such anhydrides is disclosed. The catalyst composition is prepared by an organic heterogenous technique followed by a water treatment step and activation.

7 Claims, 14 Drawing Figures

PROCESS FOR THE SYNTHESIS OF CARBOXYLIC ANHYDRIDES USING A VANADIUM, PHOSPHORUS OXYGEN CONTAINING CATALYST COMPOSITION

BACKGROUND OF THE INVENTION

This invention relates to an improved oxidation catalyst, its method of preparation, and its use in a process for the preparation of carboxylic acid anhydrides from hydrocarbons. More particularly, it relates to a novel and simpler method for the production of vanadium-phosphorus-oxygen catalyst composites providing increased yields. Still more particularly, it relates to the production of maleic anhydride from n-butane or n-butene, in a vapor phase process employing the foregoing catalyst composition.

Methods for the preparation of catalyst compositions of vanadium, phosphorus, and oxygen, and the use of these compositions as catalysts in hydrocarbon oxidations are known in the art.

Such preparative methods can be generally categorized as being aqueous-based or organic-based and employ either homogeneous solutions or heterogeneous mixtures (e.g., suspensions) of at least one of the components (e.g., a vanadium containing compound) which eventually forms the catalyst composition.

The particular method of preparation selected will depend on the various combination of properties sought to be imparted to the catalyst and the commercial attractiveness of the process. Particularly significant properties sought to be influenced by the catalyst preparative methods of the prior art include the vanadium valence, the P:V atomic ratio, the crystal phases of the catalyst, and the surface area of the catalyst.

While at least one patent seeks to impart a vanadium valence of less than +3.9, namely, U.S. Pat. No. 4,178,298, a majority of patents seek to obtain a vanadium valence between +4 and +5.

One preferred way of achieving this is to begin with vanadium in the +5 valence state and reduce the valency to less than +5 or alternatively to start with a vanadium compound having a valency of less than +5. A wide variety of reducing agents can be employed for the former reducing method approach. Representative of such reducing agents include acids such as hydrochloric, hydriodic, hydrobromic, acetic, oxalic, malic, citric, formic and mixtures thereof such as a mixture of hydrochloric and oxalic may be used. Sulphur dioxide may be used. Less desirably, sulfuric and hydrofluoric acids may be employed. Other reducing agents which may be employed are organic aldehydes such as formaldehyde and acetaldehyde; alcohols such as pentaerythritol, diacetone alcohol and diethanol amine. Additional reducing agents include hydroxyl amines, hydrazine, and nitric oxide or nitric acid.

Reducing methods also can be classified according to whether the vanadium compound is dissolved, e.g., solution reducing methods, or not, e.g., heterogeneous reducing methods.

In accordance with solution reducing methods, a vanadium compound having a valence of +5 such as $V_2O_5$ is dissolved in a solution containing the reducing agent. Because many strong acid reducing agents, such as HCl, also function to dissolve the vanadium compound and, therefore, act as a solvent, the solvent and reducing agent can be the same (see for example Kerr, U.S. Pat. No. 3,288,721). Thus, a strong acid reducing agent (e.g., HCl) can be employed in an aqueous or non-aqueous (e.g., organic) medium to achieve dissolution and reduction therein. For example, Bergman et al, U.S. Pat. No. 3,293,268 discloses an aqueous solution reduction process for preparing a V-P-O containing catalyst wherein $V_2O_5$ and phosphoric acid are dissolved and reacted in a concentrated aqueous solution of a hydrogen halide, e.g., HCl, and the resulting reaction product is heated to 300° to 500° C. to yield a catalyst having a P:V atomic ratio of 1.02:1 to 1.5:1. This patent also discloses that when n-butane is admixed with an oxygen containing gas in the presence of 3 to 50 moles of steam per mole of n-butane, the yield of maleic anhydride using the catalyst described therein is improved. However, the weight % yield of maleic anhydride from butane at reaction temperatures of 525° to 600° C. is only 25 to 52% (i.e., 14.8 to 30.8 mole % yield).

Harrison I, U.S. Pat. No. 3,915,892 also discloses an aqueous solution reduction method wherein a dihydrate catalyst precursor is formed which is subjected to rigidly controlled heating steps to form an anhydrous crystalline catalyst and bring about several phase transitions. This pretreatment procedure is complex and expensive and the maximum weight % yield from butane of maleic anhydride obtained at a reaction temperature of 465° C. is only 87.3% (i.e., a mole % yield of 51.6).

Schneider, U.S. Pat. No. 3,864,280 discloses an organic solution reduction method wherein $V_2O_5$ is dissolved in a $V_2O_5$/isobutanol slurry by passing a stream of anhydrous HCl gas into the slurry at a temperature of between 30° and 40° C. The resulting solution is then mixed with a solution of orthophosphoric acid in isobutanol and the resulting mixed solutions are heated to reflux; i.e., 110° C., for 1.5 hours. The solvent is then evaporated and the resulting catalyst precursor is activated in air, and then in an air and butane mixture. The aforenoted process is conducted to impart to the catalyst a vanadium valence of plus 3.9 to 4.6, a P:V atomic ratio of 0.9 to 1.8:1, and an intrinsic surface area (i.e., the surface area of the catalyst in the absence of a support) of 7 to 50 m²/gm. Optionally, the catalyst preparative method is conducted to impart a particular crystalline structure characterized as a B-Phase of at least 25%. To do this a minor amount of water must be present in the V-P-O isobutanol slurry used to prepare the catalyst thereby forming a hydrated precursor which looses its water of hydration upon activation bringing about the crystal phase change. The maximum weight % yield, obtained from butane at 370° C. and after an unspecified reaction time, is disclosed as being 105% (i.e., 62.1 mole % yield).

Harrison II, U.S. Pat. No. 3,982,775 discloses an organic solution reduction method using HCl as well as an organic heterogeneous method wherein the vanadium and phosphorus containing components are reacted while suspended in an organic solvent. However, it is suggested therein that the solvent must contain at least about 20% by weight water. A dihydrate precursor is formed as in Harrison I and must be subjected to the complicated activation procedures disclosed therein. The dihydrate prepared by the non-aqueous heterogeneous method exhibits a DTA (differential thermal analysis) endothermic dip at 406° C. The catalyst of Example 14 exhibits a weight % yield of maleic anhydride from butane at 418° C. and after 160 hours of reaction of 102.6% (i.e., 60.7 mole % yield) the highest disclosed in this patent.

Katsumoto et al, U.S. Pat. No. 4,132,670 discloses an organic heterogeneous reduction method wherein $V_2O_5$ is first partially reduced by refluxing in an organic media (el.g., isobutanol) for about 3 hours to reduce the average vanadium valence from +5 to about +4.5. Water formed during the reduction step may be removed by azeotropic distillation. A solution of orthophosphoric acid in isobutanol is then added to the reduced vanadium slurry and the vanadium and phosphorus components reacted at reflux temperature while removing water formed in-situ by azeotropic distillation. The resulting V-P-O suspended solids are removed from the organic medium by filtration. For fixed bed catalysts the solids are either pelleted and dried or extruded and dried. Extrusion can by achieved by adding sufficient water to the solid filter cake to form a paste, e.g., 1 part by weight water per 4.3 parts by weight solids. However, insufficient water is present during extrusion to alter catalyst properties and no extrusion temperatures are disclosed, it, therefore, being difficult to determine whether extrusion occurs at any temperature other than room temperature. Consequently, neither the amount of water nor the temperatures required to induce the catalyst properties obtainable by the water treatment step of the present invention are disclosed as being present during catalyst solids extrusion (see Example I therein). Furthermore, the catalyst of Katsumoto et al is calcined for fixed or fluid bed operations. This calcination is apparently conducted in accordance with the 2-stage activation procedure described at col. 7 lines 65 et seq. In the first stage the vanadium phosphate is heated in air at about 380° C. (flow rate 2–3 v/v/min) for about 2 hours. In the second stage the air stream is then replaced by an air-butane mixture (1.5% by vol. n-butane) at a similar flow rate and temperature for about 15 hours. The temperature and flow rate are then adjusted to achieve a conversion of 90%. Thus, activation is always conducted by contact with air alone. In contrast, the performance of the catalyst of the present invention is actually significantly diminished if activated in air alone. Maximum mole % yields of maleic anhydride from butane disclosed in this patent are about 50% at about 425° C. and 90% conversion.

Not all prior art methods employ strong acids for the purpose of reducing the average vanadium valence. For example, Hutchings et al, U.S. Pat. No. 4,209,423 (assigned to ICI Ltd.) discloses a method for preparing a V-P-O catalyst which has as its primary goal an increase in the proportion of a particular crystal phase in the catalyst designated as Phase-X and alleged to be primarily responsible for improved performance of the catalyst. The increase in Phase-X (subsequently designated in U.S. Pat. No. 4,222,945 as $\alpha$-$VPO_5$) is achieved by two essential procedures, namely, conditioning, by contacting, a catalyst precursor (i.e., the reaction product of a vanadium compound and a phosphorus compound) with an acid stronger than $H_3PO_4$, e.g., HCl, to increase Phase-X directly, and by extracting at least one water soluble crystal phase, designated as Phase-E, to indirectly increase the proportion of Phase-X by removing non-Phase-X portions of the catalyst. Thus, in one embodiment a vanadium compound, e.g., $V_2O_5$ is dissolved in a concentrated aqueous acid, e.g., HCl solvent. To this solution is added a phosphorus compound, such as orthophosphoric acid, which reacts with the vanadium compound to form a vanadium/phosphorus mixed oxide catalyst precursor. Alternatively, the $V_2O_5$ and orthophosphoric acid can be dissolved initially in the same aqueous HCl solvent, and reacted in the same pot. As a further alternative, a compound of vanadium and phosphoric acid can be reacted in the presence of water and/or a lower alcohol, e.g., methanol, (water alone being the preferred solvent) to produce a form of alpha $VOPO_4$ which is then conditioned in a solution of a strong acid to form the precursor. In all instances, a strong acid conditioning step is employed, and the conditioned precursor must be removed from an aqueous acid solution (unlike the process of the present invention which forms a heterogeneous suspension of the first catalyst precursor), e.g., by evaporation of the acid solvent. The dry or nearly dry conditioned precursor is then extracted with water or another solvent, [e.g., by boiling in water (20 ml/g solid) for 3 hours, filtered hot, washed in warm water and dried in air at 60° C.] to remove a crystal phase from the precursor identified as $VO(H_2PO_4)_2$ and designated Phase-E as described above. The precursor is then calcined in an air and butane mixture at 385° C. for 100 hours. Other properties possessed by the catalyst in addition to Phase-X, are the additional presence of Phase-B as defined in the Schneider Patent discussed above, a P:V atomic ratio of 1:0.5 to 1.2:1, and a surface area of at least 10 $m^2/g$. No mention of vanadium valence is made in this patent as being critical to cataysts performance. The maximum mole % yield of maleic anhydride from butane using an unpromoted catalyst is disclosed as being 53%, at 385° C. for an aqueous solution method (i.e. Example 3). However, in Example 7 when $V_2O_5$ and orthophosphoric acid are reacted in methanol (by refluxing), contacting the precursor with aqueous HCl, extracting the precursor with water, and calcining, the mole % yield is only 44% at a reaction temperature of 385° C. and 47% at a reaction temperature of 420° C.

Higgins et al, U.S. Pat. No. 4,222,945 (also assigned to ICI) describes a process similar to Hutchings et al, except that the mean crystallite size of the water extracted precursor is controlled within defined limits by ball milling the water extracted precursor in the presence of a solvent such as cyclohexane, preferably in the presence of a dispersant. The resulting catalyst is used to oxidize a hydrocarbon-air mixture containing at least 10 mole % hydrocarbon. Maximum mole % yield of maleic anhydride from butane is about 10%.

Generalizing from the above discussion, conventional preparative methods, including both the aqueous and organic solution techniques, are unsatisfactory in that:

(1) they usually require that the catalyst manufacturing equipment be fabricated of special corrosion-resistant materials of construction;

(2) they are troubled by serious waste-disposal problems arising out of the employment of hydrogen chloride, nitric acid or oxalic acid for the dissolution of the vanadium component;

(3) they generally require extended and complex procedures for activation of the precursor catalyst;

(4) the preparation of the precursor catalyst is generally complicated and inherently costly; and (5) the aqueous-based preparations result in catalysts of relatively poor activity and yield for converting butane to maleic anhydride.

The organic heterogeneous non-HCl method of Katsumoto et al simplifies the preparative procedures of Schneider but at the expense of drastically reduced yields. The V-P-O preparative method and water extraction technique as described and practiced in Hutchings et al also results in drastically reduced yields.

The known mixed oxide compositions for the catalytic conversion of hydrocarbons to carboxylic acid anhydrides also suffer from a number of disadvantages which include relatively poor selectivities, poor activities at low operating temperatures, poor stability manifested by short operation lifetimes, inadequate yields and a required activated procedure which is long and complicated.

Accordingly, there has been a continuing search for new and improved V-P-O containing catalysts and methods of their preparation which produce higher yields than heretofore obtainable in the prior art. The present invention is a result of this search.

SUMMARY OF THE INVENTION

In one aspect of the present invention there is provided a process for preparing a composition comprising vanadium, phosphorus and oxygen capable of catalyzing the oxydation of hydrocarbons comprising:
1. reacting a vanadium containing compound and a phosphorus containing compound in the presence of a liquid organic media in a manner and under conditions sufficient to form in said liquid organic media a heterogeneous vanadium-phosphorus-oxygen first catalyst precursor composition having an atomic ratio of phosphorus to vanadium of from about 0.5:1 to about 2:1, and an average vanadium valence of from about 3.9 to about 4.7;
2. separating said first catalyst precursor composition from said liquid organic media;
3. contacting said first catalyst precursor composition with at least one part by weight water per part by weight first catalyst precursor composition at a temperature of at least 30° C. to form a second vanadium-phosphorus-oxygen catalyst precursor composition;
4. separating said second catalyst precursor composition from said water; and
5. activating said second catalyst precursor composition.

In another aspect of the present invention there is provided a catalyst composition comprising vanadium, phosphorus and oxygen having a phosphorus to vanadium atomic ratio of from about 0.9:1 to about 1.6:1; an average vanadium valence of from about 3.9 to about 4.7; and a mid-infrared spectral pattern characterized as described herein, and preferably prepared by the process described above with the exception that activation is conducted in a non-oxidizing atmosphere.

In a further aspect of the present invention there is provided a process for oxidizing, in the vapor phase, at least one hydrocarbon feed to at least one carboxylic anhydride by contacting said hydrocarbon feed with a catalyst composition prepared by the above described process.

DESCRIPTION OF PREFERRED EMBODIMENTS

Figure 1:
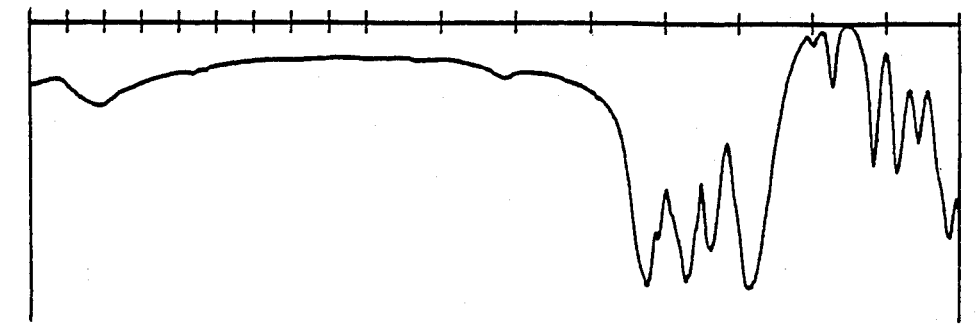
FIGS. 1 to 10 are mid-infrared spectra of V-P-O catalysts produced as described herein.

The present invention is directed to an organic heterogeneous method for preparing a vanadium-phosphorus-oxygen containing catalyst which employs a water treatment step at elevated temperatures to alter the chemical and/or physical properties of the catalyst. In addition to improving the performance of the catalyst vis-a-vis the oxidation of hydrocarbons, the process of the present invention is simple to carry out and requires a much less time consuming activation procedure. Furthermore, an embodiment of the process of the present invention is believed to produce a new and unique catalyst.

I. Preparation of the First Vanadium-Phosphorus-Oxygen Catalyst Precursor Composition In accordance with the first step of the process of the present invention, at least one vanadium containing compound and phosphorus containing compound are reacted in the presence of a liquid organic media, preferably a substantially anhydrous media, to form a first catalyst precursor. The term "media" is used herein in a collective sense to signify singular and/or plural.

The vanadium compound functions as a source of vanadium and its identity is not critical subject to the considerations described hereinafter. Accordingly, any vanadium containing compound which additionally can comprise halogen; preferably oxygen, oxygen and hydrogen, or oxygen hydrogen and carbon, may be employed. The particular vanadium containing compound selected must be capable of producing an average vanadium valence in the first catalyst precursor of between about 3.9 and about 4.7.

The initial average vanadium valence of the vanadium containing compound is preferably at least +5 although lower initial average vanadium valences of between +4 and +5, and even lower, are acceptable provided reaction conditions are controlled to impart the required average vanadium valence to the first catalyst precursor. For example, if over-reduction of the vanadium occurs, or if the average vanadium valence of the initial starting compound is below about 3.9, a suitable oxidizing agent can be employed to achieve the proper valence.

The vanadium containing compound is also selected in conjunction with the organic liquid media to be at least partially soluble therein to the extent that it can be reduced where necessary to achieve the appropriate valence as described below. Generally, the limited solubility of most known vanadium containing compounds in the organic liquid media will result in the formation of a heterogeneous suspension of the vanadium compound in that media. However, a vanadium compound, if known, which is naturally completely soluble in the organic media without the aid of strong acids, can also be employed.

Representative of vanadium compounds which can be employed in the preparation of the first catalyst precursor are vanadium oxides, such as vanadium tetroxide, vanadium pentoxide and vanadium trioxide; vanadium halides and oxyhalides, such as vanadium trichloride, vanadium tribromide, vanadyl chloride, vanadyl trichloride, vanadyl dichloride, vanadyl bromide, vanadyl dibromide and vanadyl tribromide; vanadium-containing acids, such as metavanadic acid and pyrovanadic acid; and vanadium salts, both organic and inorganic, such as ammonium metavanadate, vanadium sulfate, vanadium oxysulfate, vanadium phosphate; vanadyl formate, oxy vanadium (IV) carboxylate, vanadyl acetocetonate, vanadyl oxalate, vanadyl alkoxides, and mixtures thereof. Vanadium pentoxide is, however, preferred.

The phosphorus containing compound useful as a source of phosphorus in the first catalyst precursor is well known in the art. Suitable phosphorus containing compounds include phosphoric acid, such as metaphosphoric acid, orthophosphoric acid, triphosphoric acid and pyrophosphoric acid; phosphorus oxides, such as phosphorus pentoxide; phosphorus halides and oxyhalides, such as phosphorus oxyiodide, phosphorus pentachloride and phosphorus oxybromide; phosphorus salts such as mono-, di- and tri-ammonium phosphates; and organophosphorus compounds, such as ethyl phosphate and methyl phosphate as well as mixtures thereof.

However, the phosphoric acids, such as orthophosphoric acid and pyrophosphoric acid and mixtures thereof are preferred. More specifically, phosphoric acid generally will be employed as an aqueous solution or mixture having a concentration of typically at least 85%, preferably at least 90%, and most preferably at least 95%, by weight, based on the weight of the solution or mixture. However, substantial improvements in the performance of the catalyst can be achieved by employing substantially anhydrous phosphoric acid, e.g., orthophosphoric acid. Polyphosphoric acid is another preferred type of anhydrous phosphoric acid. This acid is commercially available as a mixture of orthophosphoric acid with pyrophosphoric, triphosphoric and higher acids, and is sold on the basis of its calculated content of $H_3PO_4$, as for example 115%. Superphosphoric acid is a similar mixture sold at 105% $H_3PO_4$. These acids revert primarily to orthophosphoric acid upon dilution with water.

The liquid organic media functions as a solvent and/or suspending agent for the vanadium containing compound, as a solvent and/or diluent for the phosphorus containing compound, and where needed, a mild reducing agent for the vanadium containing compound, and as a suspending agent for the first catalyst precursor. Thus, while any liquid organic media which is capable of performing at least one, preferably all, of the aforenoted functions can be employed, such media is preferably comprised of carbon, hydrogen, and optionally but most preferably a hetero-atom such as oxygen, nitrogen, or sulfur, and preferably is also substantially anhydrous. Included within the scope of liquid organic media are alcohols, aldehydes, ketones, ethers, amines, amides and thiols, and mixtures thereof, containing typically from about 1 to 20, preferably from about 1 to about 10, and most preferably from about 1 to about 5 carbon atoms.

More specifically, the organic moiety to which the alcohol, aldehyde, ketone, ether, amine, amide and thiol functional groups can be attached includes alkyl, typically about $C_1$ to about $C_{20}$, preferably $C_1$ to $C_{10}$, most preferably $C_1$ to $C_5$ alkyl; aryl, typically about $C_6$ to about $C_{14}$, preferably about $C_6$ to about $C_{10}$, most preferably $C_6$ aryl, cycloalkyl, typically about $C_4$ to about $C_{20}$, preferably about $C_6$ to about $C_{12}$, most preferably about $C_6$ to $C_{10}$ cycloalkyl, aralkyl and alkaryl wherein the alkyl and aryl groups thereof are described above.

Each class of liquid organic media can contain one or more, typically 1 to 3, functional groups.

The preferred organic compounds are the primary and secondary alcohols. Alcohols which contain 1, 2 or 3 hydroxyl substituent groups are especially preferred because these, in general, are readily liquified at useful temperatures in the process range. Representative hydroxylic compounds useful in the process include monoalcohols, such as methanol, ethanol, isopropanol, 1-propanol, 2-propanol, 1-butanol, isobutanol, 2-butanol, tertiary butyl alcohol, 1-pentanol, cyclohexanol, 1-octanol, 2-octanol, 3-octanol, 4-octanol, 2-hexadecanol, 2-eicosanol, 2-ethyl-1-hexanol, benzyl alcohol, etc.; di-alcohols, such as ethylene glycol, 1,4-butanediol, 1,2-propanediol; trialcohols such as glycerine, 2,2-dimethylol-1-propanol; ether alcohols such as diethylene glycol, triethylene glycol, 2-butoxy ethanol, 4-methoxybutanol, tetrahydrofurfuryl alcohol; and mixtures thereof.

Representative aldehydes include benzaldehyde, formaldehyde, acetaldehyde, propionaldehyde, m-tolualdehyde, 2-ethylhexanol, trioxane, and mixtures thereof.

Representative ketones include acetone, methylethylketone, cyclohexanone, dimethyl ketone, diethyl ketone, dibutyl ketone, methyl isopropyl ketone, methyl sec. butyl ketone, benzophenone, and mixtures thereof.

Representative ethers include diethyl ether, dibutyl ether, tetrahydrofuran, anisole, dioctyl ether, 1,2-dimethoxyethane, 1,4-dimethoxybutane, diethylene ether, and mixtures thereof.

Representative amines include ethylene diamine, hexylamine, cyclohexyl amine, diethylamine, 1,3 butadiamine, ethylene triamine, n-phenylbenzamine and mixtures thereof.

Representative amides include formamide, dimethyl formamide, acetamide, 3-butaneamide, n-phenyl acetamide, azacyclohexan-2-one, hexanediamide and mixtures thereof.

Representative thiols include phenylmethanethiol, ethanethiol, pentanethiol, 1,4-butanedithiol, cyclohexanethiol, benzylthiol, 1,5-pentane dithiol; and mixtures thereof.

The primary and secondary alkanols (ROH) having a carbon atom content in the range from 3 to 6 are a preferred class of liquid organic media for reason of cost and availability and because of their convenient boiling points. Isobutanol is the optimum liquid.

In short, any of the aforenoted liquid organic compounds alone or in any combination can be employed as the liquid organic media.

The reaction between the vanadium and phosphorus containing compounds can be achieved by a variety of methods. This reaction results in a product (designated herein as the first catalyst precursor) that is believed to be a compound which upon water treatment and activation produces the catalyst of the present invention. In this first catalyst precursor it is believed that the vanadium and phosphorus atoms are chemically bonded as opposed to being a mere mixture of oxides.

Thus, if reduction of the vanadium compound is needed, this can be achieved either in the presence or absence of the phosphorus compound.

In the first alternative (referred to herein as the 2 step vanadium treatment embodiment), the vanadium compound is admixed with a suitable liquid organic media having reducing properties and the resulting mixture heated to a temperature effective to achieve the appropriate average vanadium valence state, i.e., between about 3.9 and about 4.7 (i.e., step 1 of this embodiment). Preferably, in this embodiment, the vanadium compound is only partially reduced by heating it until vanadium valence of about +4.5 is achieved.

The vanadium reduction temperature will depend on the reducing strength of the organic media selected and can vary widely. Accordingly, while any temperature effective to reduce the vanadium compound is suitable, such effective temperatures typically will vary from about 30° to about 300° C., preferably from about 60° to about 200° C., and most preferably from about 80° to about 150° C. Preferably, the liquid organic media selected will boil at about the selected temperature so the reaction can be conducted by refluxing. Thus, when isobutanol is used as the organic media, simple refluxing at about 108° C. (1 ATM) for a period of from about 5 to about 8 hours will suffice. The reaction mixture is preferably maintained in the substantially anhydrous state by removing any water formed in-situ by azeotropic distillation or other suitable means. By "substantially anhydrous" as used herein is meant typically less than about 10%, preferably less than about 5%, and most preferably less than about 1%, by weight water, based on the weight of the organic media in the reaction mixture. Since most vanadium compounds are only slightly soluble in the organic media, the reduction reaction typically will be conducted in a heterogeneous suspension.

The liquid organic media is employed in amounts effective to achieve the appropriate vanadium reduction, where needed, to provide uniform heating of the vanadium compound, and preferably to provide a slurry which can be conveniently refluxed at the selected reduction temperature. Thus, while any effective amount of organic liquid media can be employed in the separate vanadium reduction step such effective amounts typically will constitute from about 50 to about 90% by weight, based on the combined weight of liquid organic media and vanadium compound.

In some instances, instead of reducing the vanadium compound in the organic liquid media under the above described conditions in the first step of the 2 step vanadium treatment embodiment, a vanadyl alkoxide may be formed. This vanadyl alkoxide is then used in the second step of the 2 step vanadium treatment embodiment described below.

When the separate vanadium treatment step 1 is completed, the entire mixture of liquid organic media and treated vanadium compound is preferably cooled to between about 20° and about 50° C., and combined with a solution of the phosphorus compound dissolved in a similar, preferably the same, liquid organic media to form a reaction mixture (i.e., step 2 of this embodiment). The compositional characteristics of this reaction mixture are described below in connection with the preferred one-step embodiment reaction mixture. The reaction mixture is then heated, preferably refluxed, to reduce and/or react the vanadium compound with the phosphorus compound at temperatures of typically from about 30° to about 300° C., preferably from about 60° to about 200° C. and most preferably from about 80° to about 150° C., for a period of typically from about 1 to about 50 hours, preferably from about 10 to about 35 hours, and most preferably from about 15 to about 25 hours to form the first catalyst precursor. Where partial reduction of the vanadium compound in the separate reduction step is produced, heating is preferably conducted until the vanadium attains an average vanadium valence of preferably between about 4.0 and about 4.3. The above reaction is also preferably conducted to maintain the reaction mixture in the substantially anhydrous state, preferably by azeotropic distillation to remove any water formed in-situ.

In those instances where the vanadium compound already possesses an average vanadium valence of between 3.9 and 4.7, the separate vanadium reduction step can be eliminated and the vanadium compound reacted directly with the phosphorus compound in the organic media as described above.

While the aforedescribed 2 step vanadium treatment embodiment can be employed, its use is not preferred and substantial improvements in catalyst performance can be achieved by conducting vanadium reduction and reaction of the reduced vanadium compound with the phosphorus compound in a single step. It is also preferred to avoid formation of any vanadyl alkoxide in the absence of the phosphorus compound.

In accordance with this preferred embodiment, the vanadium compound and phosphorus compound are heated in the presence of an appropriate liquid organic media in a manner and under conditions sufficient to reduce the vanadium valence to the desired state and to react the phosphorus compound with the reduced vanadium compound to form the first catalyst precursor. Thus, the vanadium compound can be premixed with sufficient liquid organic media at about room temperature (to avoid premature vanadium reaction) to suspend the former, and the resulting suspension mixed with a solution of the phosphorus compound dissolved in the organic media to form a reaction mixture. The separate preparation of the suspension and solution facilitates the dissolution of the phosphorus compound which preferably is anhydrous phosphoric acid. Alternatively, the vanadium compound and phosphorus compound can simultaneously be added to the organic media to form the reaction mixture. Thus, in this embodiment the reaction mixture will comprise at least one vanadium compound, typically in suspended form, at least one liquid organic media, and at least one phosphorus compound dissolved in the organic media. The reaction mixture can also additionally contain support materials if the catalyst is to be employed in supported form, and promoters as described hereinafter.

The molar ratio of vanadium compound to phosphorus compound, in the reaction mixture is effective to produce a first catalyst precursor having a P:V atomic ratio as defined hereinafter.

However, based on the data presented in Example 13 herein, it is believed that the initial starting atomic ratios of phosphorus to vanadium in the initial reaction mixture can affect the performance of the catalyst. These ratios are determined by the mole ratio of phosphorus compound to vanadium compound used as starting materials. It has also been observed that the P:V atomic ratio in the activated catalyst does not vary significantly regardless of the particular P:V atomic ratio present in the starting materials as admixed in the initial reaction mixture. Apparently, the manner or order in which the phosphorus and vanadium atoms are incorporated into the catalyst is at least partially dependent on the P:V ratio in the initial reaction mixture, although the amount of phosphorus and vanadium atoms incorporated into the catalyst is controlled by the stoichiometry, of the reaction and therefore remains relatively constant.

Thus, while any effective mole ratio of the phosphorus compound to the vanadium compound can be employed in the reaction mixture, such effective ratios typically will be sufficient to achieve a P:V atomic ratio of from about 0.5:1 to about 2:1, preferably from about 0.9:1 to about 1.5:1, and most preferably from about 1:1 to about 1.3:1 (e.g., 1.2:1).

The liquid organic media is present in the reaction mixture in an amount effective to reduce the vanadium compound, when needed to achieve the described valence, to suspend it and the resulting first catalyst precursor in a slurry, and thereby dilute the phosphorus compound as well as the other components of the reaction mixture to the extent that uniform heating and mixing of the reactants is possible.

The term "slurry" as used in connection with the first catalyst precursor forming step wherein the vanadium compound is reacted with the phosphorus compound is defined herein to mean a suspension wherein the solid components thereof are present therein at a solids content of typically not greater than about 50, preferably not greater than about 40, and most preferably not greater than about 25%, by weight, based on the weight of the suspension. Thus, while any effective amount of the liquid organic media can be employed in the reaction mixture, such effective amounts typically will constitute from about 50 to about 98%, preferably from about 60 to about 95%, and most preferably from about 75 to about 90%, by weight, based on the combined weight of the vanadium and phosphorus compounds and the liquid organic media.

The reaction mixture is heated to temperatures and for periods effective to cause the vanadium and phosphorus compounds to react and preferably to reduce average vandium valence to between 3.9 to 4.7, (e.g., 4.0 and 4.3). Suitable reduction is indicated to have been achieved when the color of the reaction mixture turns blue (e.g., indicative of a valence of between about 4.0 and 4.3). The identity of the liquid organic media is preferably selected so that it will reflux at the selected reaction temperature. Thus, while the reaction mixture can be heated to any effective reaction temperature, such effective temperatures will typically vary from about 30° to about 300° C. (e.g., 60° to 195° C.), preferably from about 60° to about 200° C., (e.g., 70° to 120° C.) and most preferably from about 80° to about 150° C., for periods which typically will vary from about 1 to about 50 hours, preferably from about 10 to about 35 hours, and most preferably from about 15 to about 25 hours.

The use of azeotropic distillation to remove water and any other low boiling compounds formed in-situ is preferred.

The reaction pressure for all embodiments is not critical and can be subatmospheric, atmospheric, or superatmospheric provided the reactants and liquid organic media do not volatilize to the extent that the composition of the reaction mixture is altered from the description provided herein. Atmospheric pressure is preferred.

It is also believed to be preferable to conduct the first catalyst precursor forming reaction under sufficient agitation to assure uniform reacting, and interaction between the reactants, during reaction. This can be achieved by conventional high speed agitation equipment capable of achieving a high degree of mixing.

Upon completion of the reaction, the resulting first catalyst precursor exists as a suspension of particles thereof in the liquid organic media. The reaction mixture is preferably cooled to between 20° and 50° C. and the first catalyst precursor is then separated from the liquid organic media. This separation can be accomplished in a variety of ways. Generally, it takes place in two stages, namely, by bulk separation and then final pruification, e.g., by drying.

Bulk separation can be accomplished by filtering the reaction mixture to recover the first catalyst precursor as a filter cake, by centrifuging the reaction mixture, and separating, e.g., by decanting, the supernatant liquid organic media from the solid precursor, or by evaporating the liquid organic media to form a cake or paste of the first catalyst precursor.

The precursor solids, after bulk separation, are then typically subjected to conditions sufficient to remove any residual liquid organic media. This can be achieved by drying, preferably continuous drying, to evaporate residual organic liquid media, by washing the precursor solids with water, or by employing both procedures. Before final purification is conducted, the separated first catalyst precursor solids can be washed in the liquid organic media one or more times to remove any residual unreacted phosphorus compound and/or any other organic soluble species followed by a repetition of bulk separation procedures.

Drying can be achieved by exposing the precursor to air at room temperature for a period of from about 1 to about 100 hours or by placing it in a forced hot air oven maintained at a temperature of less than about 180° C., typically between about 60° and about 150° C. for about 1 to about 5 hours. Alternatively, the precursor can be air dried at room temperature for between about 1 and about 48 hours and then placed in the forced hot air oven. Drying of the first catalyst precursor preferably should be conducted at temperatures below which crystal phase transitions occur and until a level of nearly constant weight is achieved. Drying under reduced pressure at room or elevated temperature, as described above, can also be employed as a suitable alternative.

Where a water wash is employed (generally at room temperature) no drying is needed. The resulting first catalyst precursor has an average vanadium valence of typically between about 3.9 and about 4.7, preferably between about 3.9 and 4.4, most preferably between about 3.9 and about 4.1; a P:V atomic ratio of typically from about 0.5:1 to about 2:1, (e.g., about 0.6:1 to about 2:1) preferably from about 0.9:1 to about 1.5:1, most preferably from about 1:1 to about 1.3:1. Generally the P:V atomic ratio is at least 1:1 and not more than 1.4:1.

The average vanadium valence is defined herein as the sum of the products of the mole fraction of total vanadium in each valence state times said valence, said sum covering all the valences present.

II. Water Treatment of the First Catalyst Precursor

The first catalyst precursor is then subjected to a water treatment step wherein it is contacted with a critical amount of water at elevated temperatures.

In accordance with this procedure, each part by weight of the first catalyst precursor is treated by contacting it with at least 1 part by weight water, preferably at least 2 parts by weight water, and most preferably at least 4 (e.g., at least 20) parts by weight water, at temperature of at least 30° C., preferably at least 50° C., and most preferably at least 70° C. for a period of at least 0.5 hour, preferably at least 1 hour, and more preferably at least 2 hours. Higher amounts of water and higher temperatures are permissible, although the particular amount of water above the critical limit will normally be affected by economic considerations. Thus, the weight ratio of the first catalyst precursor to water which is employed in the water treatment step typically will vary from about 1:1 to about 1:20, preferably from about 1:2 to about 1:10, and most preferably from about 1:4 to about 1:10. There is no upper limit on the amount of water used to treat the first catalyst precursor.

Water treatment temperatures (i.e., the temperature of the water upon contact with the precursor) typically will vary from about 30° to about 300° C., (e.g., 40° to 100° C.), preferably from about 50° to about 150° C., and most preferably from about 70° to about 150° C.

If the amount of the water which is contacted with the precursor is less than 1:1, insufficient changes occur in the first catalyst precursor, and while the final catalyst will result in oxidation of the hydrocarbon, the particular catalyst of the present invention will not be produced. Evidence of the criticality in the amount of water is provided in the examples. The elevated temperature is critical in that it renders the water treatment step capable of being completed within a reasonable period of time.

Thus, at the aforedescribed temperatures, the water treatment contact period will typically vary from about 0.5 to about 100 hours, preferably from about 1 to about 50 hours, and most preferably from about 2 to about 25 hours.

The method of water contact can vary and is not critical. Thus, the first catalyst precursor can be slurried in water in a reaction vesssel equipped with a stirrer, and heated or refluxed, for the disclosed contact times and temperatures.

Alternatively, the first catalyst precursor can be placed in a water wash drum wherein hot water is continually passed into the drum over the precursor, and out the drum.

The first catalyst precursor can also be first shaped into a desired structure, such as by extruding a water wet paste of the precursor to form pellets, by compressing to form tablets, and the like, or deposited on a support, and the shaped precursor then placed into a reactor tube through which is passed steam, typically at a temperature of from about 100 to about 300, preferably from about 100 to about 250, and most preferably from about 100° to about 180° C. The shaped and steam treated first catalyst precursor referred to herein as the second catalyst precursor (i.e., fresh catalyst) can then be activated (as described hereinafter) directly to form the final catalyst since the steam treatment will typically result in the production of a dry fresh catalyst. Drying of the steam treated second catalyst precursor composition can also optionally be conducted.

After water treatment, the non-shaped second catalyst precursor is separated from the water by any of the aforedescribed bulk separation and drying techniques described above.

Improved results are obtained by the evaporation bulk separation technique in terms of the performance of the catalyst. However, care should be taken to conduct evaporation of the aqueous media in a uniform manner, i.e., by avoiding uneven heating of the precursor, otherwise, for reasons not yet fully understood, the final catalyst will not perform in an optimum manner. Thus, evaporation should be conducted under mild agitation taking steps to avoid caking of the precursor on the walls of the evaporation vessel which leads to uneven heating. Sufficient aqueous media preferably should remain at the completion of vat evaporation to avoid the creation of hot spots in the precursor. This can be achieved by evaporating the suspension of second catalyst precursor to a solids content of typically from about 15 to about 60, preferably from about 15 to about 50, and most preferably from about 20 to about 40% by weight, based on the weight of the resulting solid liquid mixture. A more commercial approach to evaporation is to use thin film evaporation or a spray drying technique. One type of thin film evaporator comprises a rotating drum equipped with a scrapper blade and means for heating the surface of the drum. The drum is then inserted into the agitated reaction mixture and rotated. A thin film of the slurry is picked up on the surface of the drum and the liquid organic media is evaporated leaving precursor solids on the drum's surface. The scrapper blade then removes the precursor solids from the drum's surface. This leads to uniform heating and evaporation. Spray drying is preferred for catalysts employed in fluidized bed operations.

The rate of evaporation is also believed to affect the performance of the catalyst. Thus, the aqueous media preferably is evaporated at a rate sufficient to achieve the above-described water contact times. Accordingly, the application of pressures below atmospheric can be employed to facilitate evaporation where atmospheric conditions are such that the reduced pressures facilitate attaining the appropriate evaporation rate.

Evaporation temperatures typically will be the boiling point of the aqueous media although evaporation at temperatures between said boiling point and room temperature under vacuum can be employed.

The first catalyst precursor after the water separation step is also referred to herein as the second catalyst precursor or alternatively as fresh catalyst.

It is to be understood that the water employed in the water treatment step can contain additional, beneficial components.

Thus, in an alternative embodiment it may be useful to conduct the water treatment step using water having vanadium-phosphorus oxides dissolved therein. To do this, an aqueous vanadium-phosphorus oxide solution is prepared by first reducing $V_2O_5$ with a suitable reducing agent such as HCl or oxalic acid in water. When the solution turns blue, phosphoric acid, e.g., aqueous 85% $H_3PO_4$, is added to the solution. It is then refluxed or simply stirred and heated to obtain a vanadium-phosphorus-oxygen aqueous solution. The ratio of P/V in the aqueous solution is preferably the same as in the aforedescribed first catalyst precursor preparation method. The resulting solution is then used to conduct the water treatment step. The weight of V-P-O in solution can be as high as the weight of first catalyst precursor to be treated.

Upon completion of this modified water treatment step, the water or water and dissolved V-P-O is preferably separated from the precursor using bulk separation techniques described above.

III. Activation of the Fresh Catalyst

The fresh catalyst must be activated in order to produce a final catalyst capable of exhibiting the improved yields illustrated herein. Activation, i.e., heating of catalyst in a selected atmosphere at a selected elevated temperature, can be accomplished in a separate step or insitu in the reactor in which it will be used for the oxidation of hydrocarbons. Activation temperatures will vary slightly depending on whether the final catalyst will be employed for fixed bed or fluidized bed operations. Thus, for fixed bed operations, activation temperatures typically will vary from about 250 to about 450, preferably from about 300 to about 410, and most preferably from about 350° to about 410° C. For fluidized bed operations, the aforedescribed temperature ranges are reduced by about 50° C. Thus, activation temperatures in general can vary from about 200 to about 450, preferably from about 250 to about 410, and most preferably from about 300° to about 410° C.

The atmosphere in contact with the fresh catalyst during activation will affect the performance of the catalyst. While activation can be conducted in air alone and then in a mixture of air and a suitable hydrocarbon, the catalyst performance will suffer significant reductions in yield by this activation method.

Thus, for optimum catalyst performance, activation must be conducted in at least a non-oxidizing, preferably a partially reducing atmosphere in relation to the vanadium. More specifically, it is advantageous that the vanadium of the fresh catalyst not be oxidized during activation. A "non-oxidizing atmosphere" as defined herein does not include air alone.

Representative examples of suitable non-oxidizing atmospheres comprise: a mixture, preferably a non-explosive mixture, of air and/or inert gas (as described below) and any hydrocarbon, preferably any hydrocarbon, described hereinafter which can be oxidized in accordance with the process of the present invention for using the catalyst; hydrogen; a mixture of hydrogen and an inert gas such as $N_2$, steam, helium, argon and mixtures thereof; carbon monoxide, or a mixture of carbon monoxide and any of the aforedescribed inert gases; a mixture of carbon dioxide and any hydrocarbon as described above; a mixture of inert gas and any hydrocarbon described above; and, any hydrocarbon described above alone.

Generally, the activation atmosphere will conveniently comprise a non-explosive mixture of air and the hydrocarbon to be oxidized by the catalyst.

Preferred hydrocarbons for use in activation include methane, butane, butene, butadiene and pentane.

The mole fraction of gaseous components in the activation atmosphere typically will be outside the explosive limits of the mixture.

Thus, when the activation atmosphere comprises air and butane, such mixtures preferably will contain, for example, between about 0.1 to about 1.8 (e.g., 1.0 to 1.2) mole % butane or above about 24 mole % butane.

Although not essential, it is desirable to maintain a steady flow of the activation atmosphere over the fresh catalyst surface during activation. Flow rates typically will be sufficient to provide a contact time with the catalyst of about 1 to about 10, preferably from about 1 to about 5, and most preferably from about 1 to about 3 seconds. Thus, suitable flow rates or "space velocities" of the activating atmosphere may be manipulated by one skilled in the art to achieve the desired contact time.

The period of activation will depend on the particular activation temperature and atmosphere selected as well as the [activation atmosphere] contact time. Generally, such activation periods at the aforedescribed activation temperatures and in the presence of a non-oxidizing atmosphere will typically vary from about 0.5 to about 72, preferably from about 1 to about 48, most preferably from about 1 to about 24 hours.

The preferred method of activation is to place the fresh catalyst in the reactor in which it will be employed and pass a gaseous mixture of air and butane in continuous flow over the fresh catalyst at temperatures of between about 390° and 410° C. until the conversion of the butane reaches about 90% on a molar basis. The temperature of the feed stream is then lowered to reaction temperature and product produced as desired. Thus, this activation procedure is simple and easy to achieve and actually produces collectable product during the course thereof.

IV. Catalyst Shaping

At some point in their preparation, the catalysts described herein preferably are formed into structures suitable for use in a reactor, although unshaped, powder catalyst can be employed. Techniques for forming the appropriate structures for use in a fixed bed reactor or a fluidized bed reactor are well known to those skilled in the art.

For example, the catalyst can be structured in unsupported form for use in fixed bed reactors by prilling or tableting, extruding, sizing and the like. Suitable binding and/or lubricating agents for pelleting or tableting include Sterotex ®, starch, calcium stearates, stearic acid, and graphite. Extrusion of the catalyst can be achieved by forming a wet paste which does not slump and extruding the paste.

Supported catalysts for use in either fixed or fluidized bed operations employ carriers including alumina, silica, silica gel, silica-alumina, silicon carbide, ceramic donuts, magnesium oxide, titania and titania-silica. Spray dried catalysts can also be employed for fluidized bed operations.

The preferred shape for fixed bed operations is a cylindrical pellet having a hollow core running through the center thereof.

A catalyst support, if used, provides not only the required surface for the catalyst, but gives physical strength and stability to the catalyst material. The carrier or support typically possesses a surface area of from about 0.1 to about 200, preferably from about 1 to about 50, and most preferably from about 5 to about 30 $m^2/g$. A desirable form of carrier is one which has a rough enough surface to aid in retaining the catalyst adhered thereto during handling and under reaction conditions. The support may vary in size but generally is from about 2½ mesh to about 10 mesh in the Tyler Standard screen size. Alundum particles as large as ¼ inch are satisfactory. Supports much smaller than 10 to 12 mesh normally cause an undesirable pressure drop in the reactor, unless the catalysts are being used in a fluid bed apparatus.

The support material is not necessarily inert, that is, the particular support may cause an increase in the catalyst efficiency by its chemical or physical nature or both.

The amount of the catalyst deposited on the support is usually in the range of about 5 to about 90, preferably from about 5 to about 80% by weight based on the combined weight of catalyst and support. The amount of the catalyst deposited on the support should be enough to substantially coat the surface thereof and this normally is obtained with the ranges set forth above. With more absorbent carriers, larger amounts of material will be required to obtain essentially complete impregnation and coverage of the carrier. In a fixed bed process, the final particle size of the catalyst particles which are coated on a support will also preferably be about 2½ to about 10 mesh size. The supports may be of a variety of shapes, the preferred shape of the supports is in the shape of cylinders or spheres.

The particle size of a supported or unsupported catalyst used in fluidized beds is quite small, usually varying from about 10 to about 200 microns. Typically the attrition resistance of such catalysts is improved by the presence of zirconium or other modifier capable of hardening the catalyst. This can be achieved by the addition of oxides of the appropriate metal during preparation of the first catalyst precursor or during the water treatment step.

Inert diluents such as silica or $TiO_2$ may be present in the catalyst, but the combined weight of the essential active ingredients of vanadium, oxygen and phosphorus should preferably consist essentially of at least about 10, preferably at least about 30% by weight, based on the total weight of catalyst and support.

Shaping of unsupported catalyst can be conducted prior to steam treatment (of the water treatment step), and prior or subsequent to activation of the fresh catalyst. Preferably, shaping of the unsupported catalyst is conducted on the fresh catalyst prior to activation. The point during which shaping with supports or carriers is conducted will vary with the type of support. For example, silica supports can be added during the water treatment step.

Solid supports, such as silica alumina, can be added to the reaction mixture during the formation of the first catalyst precursors, the water treatment step, or subsequent to the water treatment step.

V. Stability Additives

In addition to vanadium, phosphorus, and oxygen, the catalyst of the present invention may also comprise effective amounts of stability additives which have been designated herein as promoters and/or activators. The typical additives which are used include magnesium, calcium, scandium, yttrium, lanthanum, uranium, cerium, chromium, manganese, iron, cobalt, nickel, copper, zinc aluminum, gallium, indium, silicon, germanium, tin, bismuth, antimony, tellurium, lead, titanium, hafnium, lithium, potassium, cesium, zirconium, and mixtures thereof.

The promoters and/or activators are readily introduced into the catalyst during formation of the first catalyst precursor by admixture with the vanadium and phosphorus compounds during the heating in the organic liquid media. These promoter and activator compounds, however, should be at least partially soluble in the solvent medium used in the particular preparation in order to be best suited for combination with the phosphorus and vanadium components of the catalyst. Typical compounds of titanium, which is the preferred activator, include titanium oxides, such as titanium oxide, titanium dioxide, titanium trioxide, titanium sesquioxide, titanium pentoxide, titanium halides such as titanium dichloride, titanium trichloride, titanium tetrachloride, titanium dibromide, titanium tribromide, titanium diiodide, titanium triiodide, titanium tetraiodide, and titanium tetrafluoride; titanium salts such as titanium phosphates and titanium sulfates; and organic titanium compounds, e.g., alkyl titanates such as methyl titanate, ethyl titanate, isopropyl titanate and butyl titanate and aryl titanates such as phenoxy titanium trichloride and phenyl titanate. Typical compounds of zinc (illustrative of activators as a class) are metallic zinc, zinc oxide, zinc chloride, zinc bromide, zinc iodide, zinc formate, zinc nitrate or zinc acetate.

VI. Catalyst Composition

The aforedescribed process of the present invention is believed to produce a unique and novel catalyst composition not heretofore capable of being produced by prior art methods. The uniqueness of this catalyst is reflected in the substantially improved yields described hereinafter in the examples. While the reason for this improvement is not yet entirely understood, the results speak positively for themselves. The catalysts which produce these high yields have been analyzed in an attempt to determine the significant differences between the catalysts of the prior art and those of the present invention.

Accordingly, while not wishing to be bound to any particular theory, the following discussion is offered as an explanation of the effect of the water treatment step and activation as employed in the above-described process on the catalyst of the present invention. A summary of the properties possessed by the fresh catalyst and activated catalyst is also provided.

The activated catalysts of the present invention possess crystalline and non-crystalline (i.e. amorphous) portions or regions. Based on x-ray diffraction analysis a majority of the crystalline portion is believed to constitute B-Phase, a limited characteristic x-ray spectrum of which is described in Schneider U.S. Pat. No. 3,864,280. However, in the Schneider patent the method for determining the % B-Phase employs a technique wherein ratios between the height of peaks generated by an alpha-alumina internal standard and peaks generated by the catalyst are implicitly compared to an unspecified B-Phase standard. However, this unspecified standard cannot be representative of pure B-Phase because catalysts analyzed by this method have been found to possess a % B-Phase substantially in excess of 100%. Furthermore, there is no indication in the Schneider patent that the catalyst described therein possess any amorphous regions at all. Consequently, it appears that the quantification of B-Phase in Schneider at the most is an attempt to identify the relative proportion of the total crystalline structure of the catalyst which constitutes B-Phase.

When an attempt was made to compare only variations in crystallinity of the activated catalyst with variations in yield of maleic anhydride using x-ray diffraction analysis, it has been difficult to explain such variations as being solely attributable to either a direct or inverse relationship between these two isolated parameters. Consequently, it was further concluded that variations in the amorphous portion of the catalyst may be related and contribute to variations in maleic anhydride yield. However, while x-ray diffraction analysis is suitable for examining and characterizing the crystal portions of a catalyst, it reveals little or nothing about changes and/or properties of the amorphous portions thereof. Consequently, it is possible for two catalysts to exhibit similar x-ray diffraction spectra but differ completely in relation to the nature of the amorphous regions of the catalysts and vice versa.

An analytical method more suitable for distinguishing structural variations in the amorphous portions of the catalyst is mid-infrared spectroscopy. While mid-infrared spectroscopy can detect and distinguish pure crystalline phases generally, the nature of the catalysts of the present invention and of the prior art in most instances causes spectral interferences to the extent that certain crystalline phases, e.g., B-Phase, are not distinguishable unless present in high proportions.

In view of the above, distinctions between various V-P-O catalysts of the present invention and those of the prior art have been compared by observing the mid-I.R. spectra thereof.

It is at least by this I.R. analytical method that distinctions between catalysts of the present invention and those of the prior art have been found to exist.

However, not only are the catalysts of the present invention believed to be distinguished from prior art catalysts on a qualitative basis using the I.R. analytical method, but these catalysts are also believed to be more amorphous than prior art catalysts tested. This conclusion is based on several observations and assumptions drawn from both x-ray diffraction analysis and mid-infrared spectroscopy.

More specifically, it has been observed from x-ray diffraction analysis of the catalysts of the present invention, that on a qualitative basis, B-Phase constitutes the predominant, and in fact what appears to be the only detectable, crystal phase of the crystalline portion of these catalysts. Consequently, the need arose for a method for reasonably quantifying the amount of B-Phase relative to the amount of the total catalyst as a way of characterizing the catalyst. Such a method would also provide a basis on which to assign relative values of amorphous content thereto, as a way of expressing the absence of other x-ray detectable crystalline phases.

However, as described above, the prior art methods for determining % B-Phase fail to specify a B-Phase standard which could be used for determining % B-Phase based on the total weight of the catalysts. Consequently, in an effort to more accurately characterize the amount (i.e., %) of B-Phase relative to the total catalyst of the present invention, not just the crystalline portions thereof, what is believed to be pure B-Phase based on x-ray diffraction analysis data reported in the literature has been prepared to act as a standard both for purposes of x-ray diffraction analysis and mid-I.R. analysis. [See, Bordes, E., Doctorate Thesis: "The Structural Properties of the Catalytic Phases in the Stationery State. Application to the Systems V-P-O, V-Mo-O, U-Mo-O Selective for the Oxidation of Butene to Maleic Anhydride", University de Technologic de Compiegne (1979); and Bordes, E., Courtine, P., "Some Selectivity Criteria In Mild Oxidation Catalysis V-P-O Phases in Butene Oxidation to Maleic Anhydride", 50 J. Catalysis 236 (1979);]. Thus, the data reported herein relating to % B-Phase is based on the assumption that this standard theoretically represents 100% B-Phase. Based on this standard and the method for determining B-Phase described herein the activated catalysts of the present invention on a weight basis have been found to typically comprise less than 10% B-Phase. Furthermore, by using this pure B-Phase as a standard, it has been observed that B-Phase is not detectable in the catalysts of the present invention when they are analyzed by mid-infrared spectroscopy.

Accordingly, based on the observations that in the catalysts of the present invention, (1) crystalline phases other than B-Phase are not detectable and recognizable by x-ray diffraction analysis; (2) the amount of B-Phase which is detectable by x-ray diffraction analysis in conjunction with the pure B-Phase standard, does not exceed about 10%, and (3) the presence of B-Phase is not detectable by mid-infrared spectroscopy; it has been concluded that the catalysts of the present invention are predominantely amorphous, i.e., they have been assigned an amorphous content of typically greater than about 90%, preferably greater than about 93%, and most preferably greater than about 95% (e.g., greater than about 97%), by weight, based on the total weight of the catalyst. The term "amorphous" as applied to a V-P-O catalyst is defined herein to describe those portions of a catalyst not detectable and recognizable as distinct crystalline phases by x-ray diffraction analysis. It is acknowledged that this definition of "amorphous" differs from the conventional meaning of "amorphous" namely, non-crystalline; or having no molecular lattice structure. However, because of inherent limitations in the resolution of the x-ray diffraction analytical method, as described and performed herein, it is impossible to rule out the possible presence of areas or domains of molecular lattice structure in the subject catalysts which possess sufficient order to characterize them as crystalline in a technical sense, but are insufficient in terms of order and/or concentration to render them detectable as distinct, recognizable crystalline phases. For purposes of discussion, such areas or domains of non x-ray detectable and recognizable crystallinity are referred to herein as pseudo-crystallinity. Therefore, the term "amorphous" as defined herein and applied to the subject catalysts, by necessity is intended to include not only non-crystalline, but also pseudo-crystallinity, if in fact such pseudo-crystallinity is present in a catalyst sample. In short, the amorphous content is that proportion of the catalyst less the proportion of x-ray detectable and recognizable crystalline phases. It is for these reasons that the amorphous content is an assigned precentage based on the assumptions described herein. Furthermore, in the event methods for distinguishing between conventional amorphicity and pseudo-crystallinity are forthcoming, one can easily confirm or deny the belief that the catalysts of the present invention are predominantly amorphous also in a conventional sense. For example, the assigned value of amorphous content and actual amorphous content, as understood in a conventional sense, increasingly approach one another as the % of pseueo-crystallinity decreases.

Figure 6:
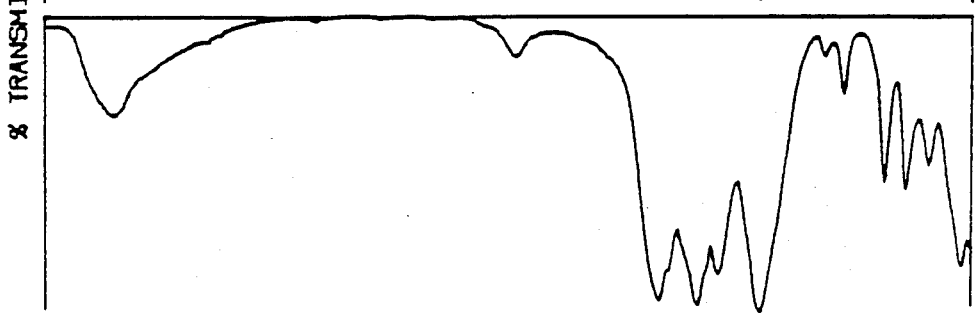
Figure 7:
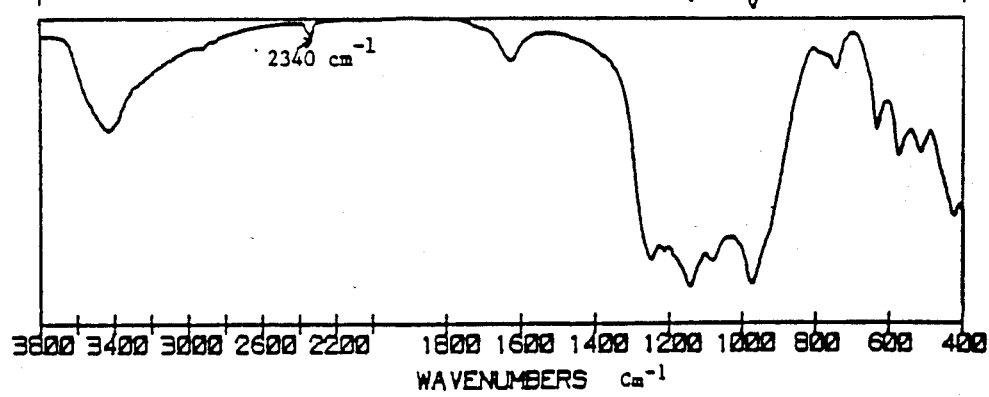
Figure 8:
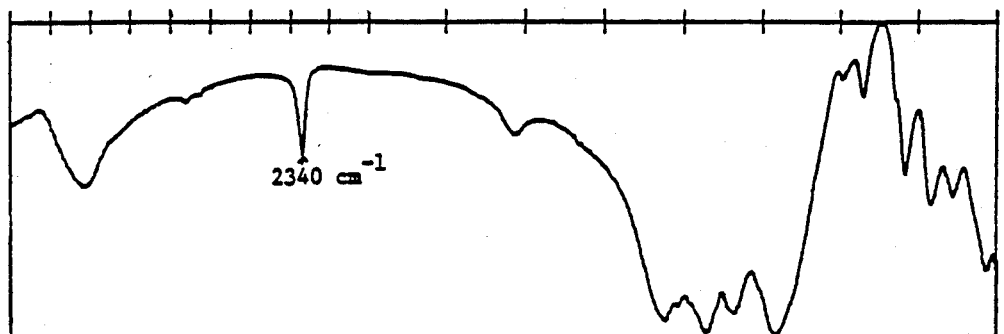

Referring to the drawings, FIGS. 1 to 8 illustrate infrared spectra of activated catalysts. The procedures for preparing the catalysts which produced these spectra are described in Examples 5, 6, 14, 16–18 and Comparative Example 7, the particular FIGURE, associated catalyst, and preparative procedure being summarized at Table A. The catalyst of FIG. 8 is derived from a preparative procedure which represents a modification in the preparative procedure disclosed in Schneider U.S. Pat. No. 3,864,280, the modification being activation in air and butane rather than air alone.

Figure 9:
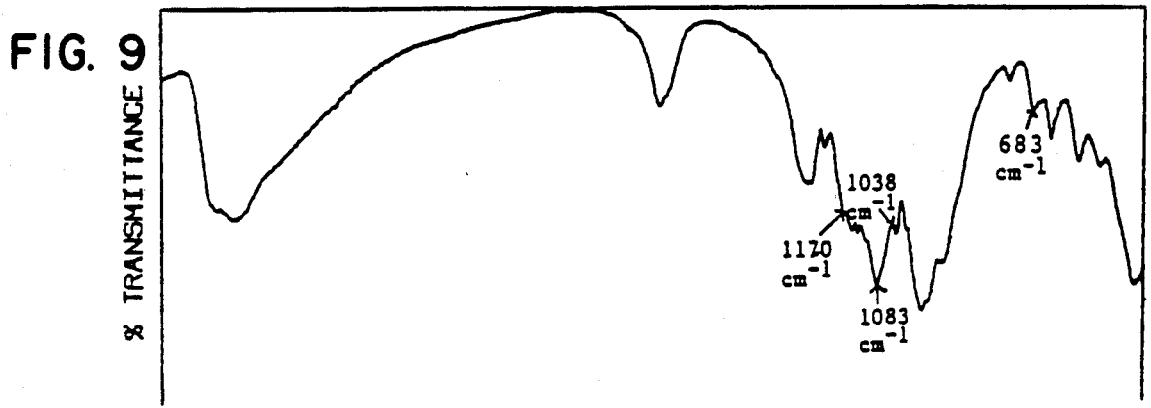
Figure 10:
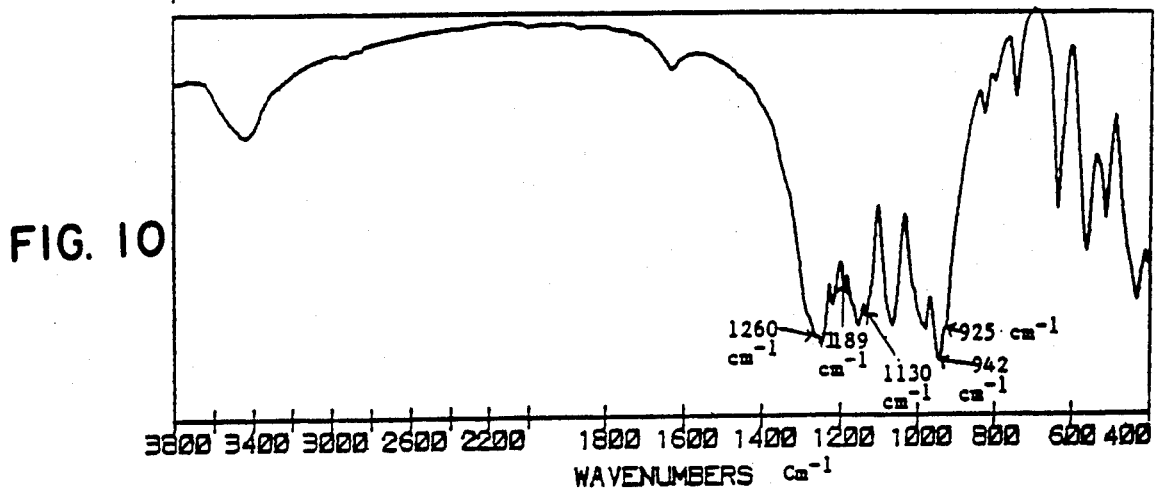

FIGS. 9 and 10 illustrate infrared spectra produced by catalysts prepared generally in accordance with the prior art, namely Katsumoto et al U.S. Pat. No. 4,132,670, (FIG. 9), and Harrison U.S. Pat. No. 3,915,892 (FIG. 10).

The method used to prepare the catalysts associated with FIGS. 9 and 10 is provided in Comparative Examples 3 and 6, the particular FIGURE, associated catalyst and catalyst properties being also summarized at Table A.

TABLE A

| FIG. No. | Preparative: Example or Comparative Example No. | Hours on Stream Before Testing IR, B-Phase, and Used P:V Ratio | P:V Ratio Fresh Catalyst | P:V Ratio Used Catalyst | % B-Phase | M.A. Yield |
|---|---|---|---|---|---|---|
| 1 | Ex. 6 | 504 | 1.17:1 | 1.02:1 | 7.1 | 64 |
| 2 | Ex. 5 | 240 | 1.07:1 | 1.01:1 | 3.6 | 64–65 |
| 3 | Ex. 5 | 220 | 1.12:1 | N/D | N/D | 63–64 |
| 4 | Ex. 14 | 530 | 1.07:1 | 1.12:1 | NA | 63–64 |
| 5 | Ex. 16 | 212 | 1.14:1 | 1.08:1 | 5.7 | 59–60 |
| 6 | Ex. 17 | 242 | 1.15:1 | 1.02:1 | 18.4 | 56–57 |
| 7 | Ex. 18 | 320 | 1.12:1 | 1.07:1 | 4.2 | 52 |
| 8 | C. Ex. 7 | 456 | 1.25:1 | 1.25:1 | 3.3 | 52 |
| 9 | C. Ex. 3 | 384 | N/D | N/D | 4.0 | 47 |
| 10 | C. Ex. 6 | 648 | N/D | 1.20 | 15.2 | 35 |

Figure 11:
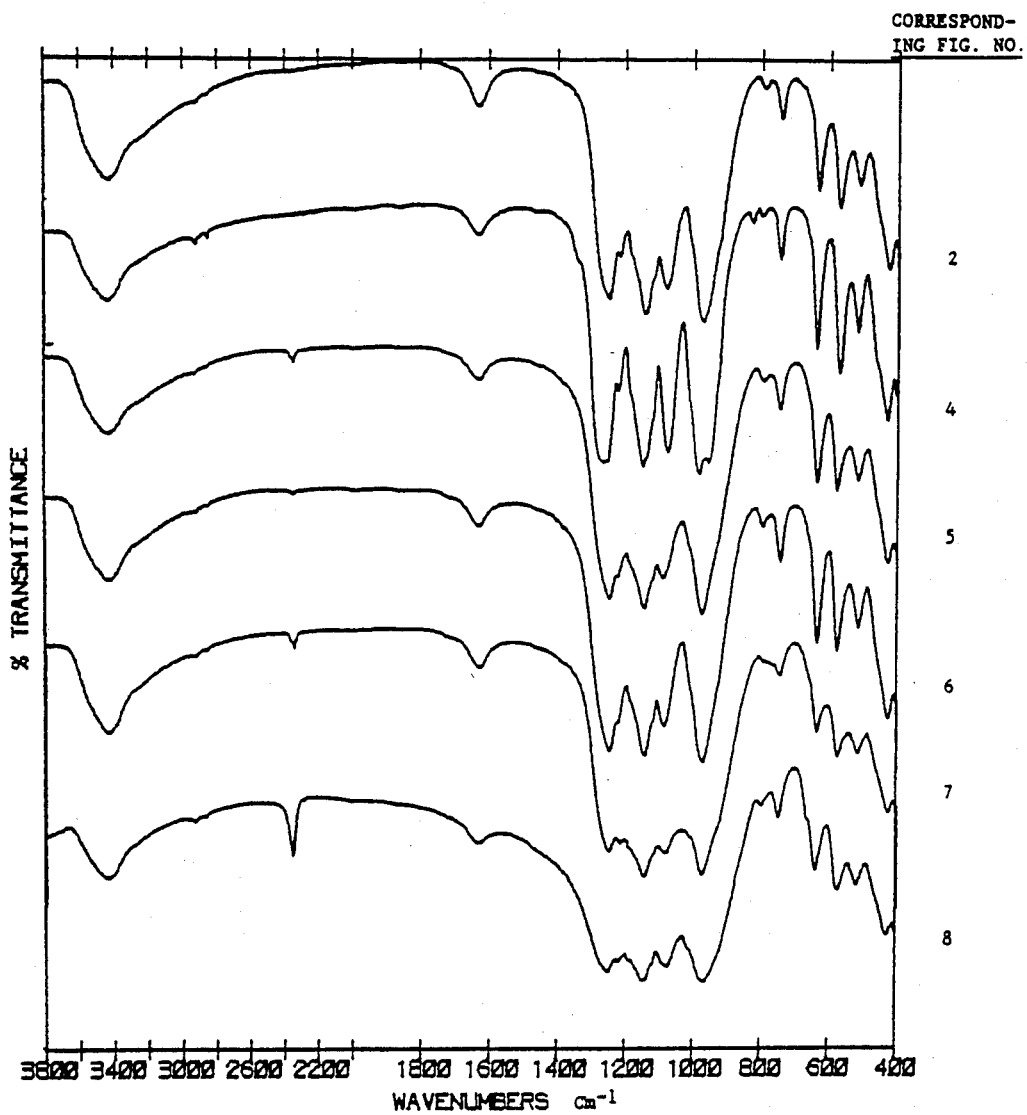
FIG. 11 depicts FIGS. 4 to 8 on the same drawing as FIG. 2, the FIG. No. corresponding to FIGS. 2, and 4 to 8 being provided in the right hand margin of FIG. 11.
Figure 12:
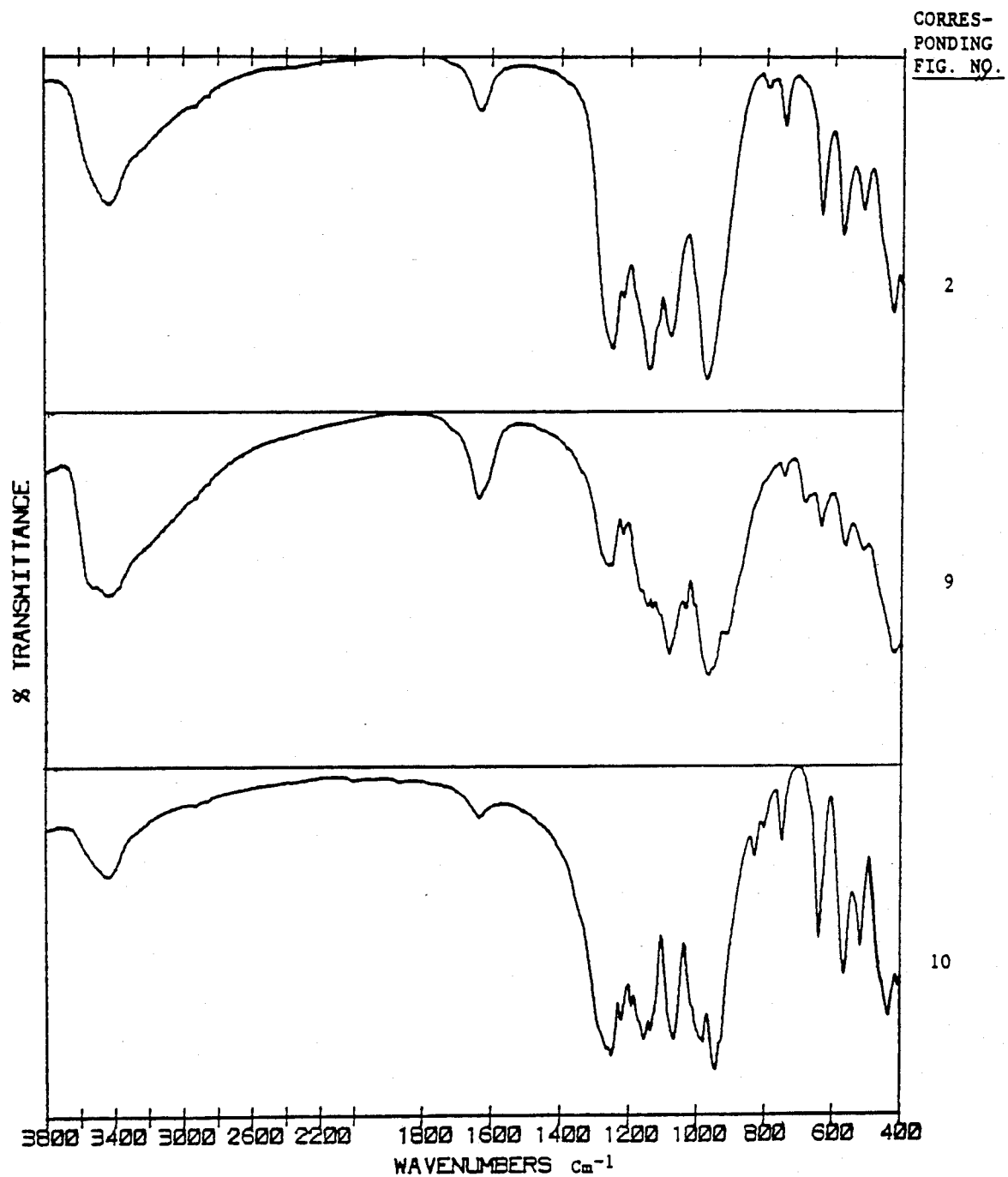
FIG. 12 does the same for FIG. 2 and FIGS. 9 and 10.

N/D = not yet determined
NA = not available due to interference of sample peak with alpha alumina standard peak.
Ex. = Example; C. Ex. = Comparative Example FIG. 11 superimposes the spectra of FIG. 2 and FIGS. 4 to 8 on the same plot to contrast one against the other. FIG. 12 superimposes the spectra of FIG. 2 and FIGS. 9 and 10 in a similar fashion.

Figure 2:
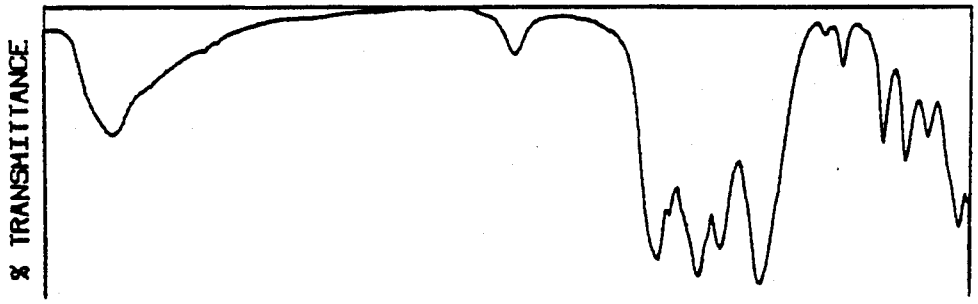
Figure 3:
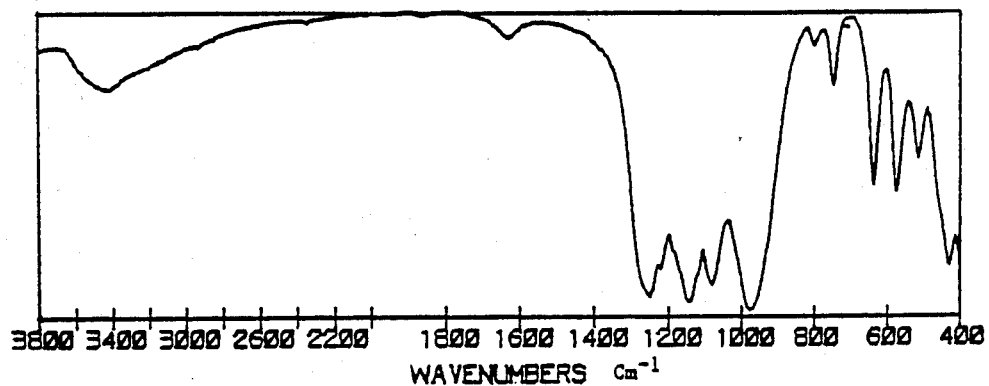

The I.R. spectra of FIGS. 1 to 3 are believed to be representative of the I.R. spectra produced by the catalysts of the present invention and are associated with yields of maleic anhydride of at least 63%. Thus the catalysts of the present invention exhibit a preferred characteristic mid-infrared spectral pattern as listed in Table B below:

TABLE B

| $Cm^{-1}$ | Intensity* |
|---|---|
| 1250 | S–VS |
| 1219 | M |
| 1145 | VS |
| 1079 | S |
| 973** | VS |
| 797 | VW |
| 745 | VW |
| 635 | W |
| 572 | W |
| 513 | W–VW |
| 426 | M–S |
| 402 | M |

*Intensity expressed as % absorbance relative to 973 $cm^{-1}$ equals 100%. Intensity is divided according to the following % ranges.
VS = 80–100%
S = 60–79.99%
M = 40–59.99%
W = 20–39.99%
VW = 1–19.99%
Note also that when more than one intensity range is provided the intensity range with the greatest probability is expressed first.
**May appear as a doublet with the second maxima at 980 $cm^{-1}$.

By "mid infrared spectral pattern" as used herein is meant one which is generated by the following procedure: one mg of catalyst sample is admixed with 200 mg of KBr. This admixture is ground for 2 minutes with a steel ball (about 3 mm diameter) using a shaker mill. The ground admixture is placed into a dye and pressed into a pellet 13 mm in diameter and 1 mm thick. The pellet is then placed into a Digilab ® fourier transform infrared spectrometer. The spectrometer is run at 4 $cm^{-1}$ resolution with undersampling (UDR=2) and no gain ranging (GRR=0). 200–500 scans are accumulated for signal averaging. An empty beam serves as reference. The spectrum is computed using phase correction (SMI=256, SMN=1024), Triangular apodization (APD=1P, BRK=0,0,0,1), and one level of zero filling (ZFF=2). Transmission spectra are obtained from a ratio of the catalyst and empty beam reference spectra over the 3800 $cm^{-1}$ to 400 $cm^{-1}$ region.

Spectral intensity is determined relative to a linear base line between 710 and 1800 $cm^{-1}$ and normalized relative to the strongest band occuring at about 973 $cm^{-1}$.

The % B-Phase in the catalysts generating FIGS. 1 and 2 is 7.1% and 3.6% respectively.

For purposes of discussion, the substantially identical I.R. spectra patterns of FIGS. 1 to 3 are said to represent a phase designated herein as Phase-Z, the characteristic peaks of which are summarized at Table B.

Figure 4:
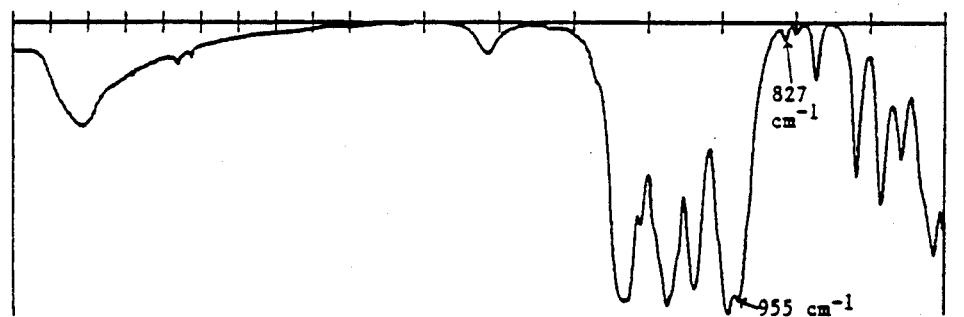

Comparing the spectral pattern of Phase-Z with that of FIG. 4 it can be seen that they are quite similar with the exception of the appearance of an additional phase as illustrated by the peaks at 827 and 955 $cm^{-1}$.

It is believed that these peaks collectively are representative of the species $VO(PO_3)_2$. This species is believed to be present in amorphous form based on the absence of corresponding peaks associated with this species upon x-ray diffraction analysis. The $VO(PO_3)_2$ species is believed to be slightly less active than pure Phase-Z. Thus, while the $VO(PO_3)_2$ species Phase-Z to some extent, the yield does not drop significantly.

Accordingly, while the catalysts of the present invention may include such additional species it is preferred that they do not. Consequently, FIG. 4 represents a less preferred catalyst of the present invention, although its spectrum is also believed to be characteristic of these catalysts, and it is not intended herein to exclude peaks at 955 and 827 $cm^{-1}$ from the characteristic spectra described at Table B.

Figure 5:
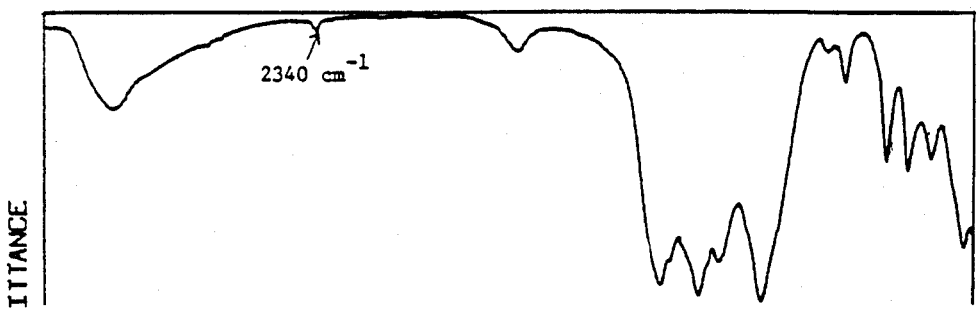

Comparing the spectra of Phase-Z with FIG. 5 it can be seen that an additional phase appears in FIG. 5 represented by a peak at 2340 $cm^{-1}$. This peak is believed to be characteristic of a P-H and/or P-OH bond containing species such as $HPO_3^-$, $H_2PO_2^-$, or $H_2PO_4^{-2}$, collectively referred to herein as P-H for purposes of discussion. The yield associated with the catalyst which generated FIG. 5 is 59–60%. In contrast a peak at 2340 $cm^{-1}$ is absent in Phase-Z. Thus, a P-H bond containing species is believed to be significantly less active than pure Phase-Z. Consequently, the catalyst of the present invention is also preferably characterized by the absence in the I.R. spectrum thereof of a peak at 2340 $cm^{-1}$. The B-Phase of the catalyst represented by FIG. 5 is 5.7%.

Comparing the spectra of Phase-Z with that of FIG. 6 it can be seen that they are quite similar with only a very small peak at 2340 $cm^{-1}$. It is not believed that this peak alone would account for the reduction in yield to 56 to 57% in relation to the catalysts of FIGS. 1 to 3.

However, the % B-Phase of the catalyst of FIG. 6 is 18.4%. Accordingly, it is concluded that it is the combined presence of a small amount of P-H bond containing species and high % B-Phase which accounts for the low yield associated with this catalyst. Consequently, based on these observations the catalysts of the present invention are also preferably defined in terms of limits on B-Phase content as described hereinafter.

The low yields associated with the spectrum of FIGS. 7 (i.e. 51–52%) and 8 (i.e. 52%) are also believed to be attributable to the P-H bond containing species. Note also that deterioration in the resolution of the peaks of the spectrum also appears to be associated with the presence of the P-H bond containing species. Note further, however that the method of preparation of the catalyst of FIG. 8 finds no counterpart in the prior art.

Comparing the spectra of Phase-Z with that of FIG. 9 (catalyst prepared in accordance with Katsumoto et al) it can be seen that the spectra are quite different, and bear very little relationship to one another. For example, note the appearance of peaks at 1170; 1083; 1038; and 683 cm$^{-1}$ in FIG. 9, which are absent in FIGS. 1 to 3. These peaks are collectively characteristic of the species VOPO$_4$.2H$_2$O (i.e. hydrated X-Phase). Note that other I.R. pellet preparations for the catalyst of FIG. 9 show an additional peak at 607 cm$^{-1}$ which is characteristic of Phase-X, i.e., α-VPO$_5$ and more appropriately written as α-VOPO$_4$. It is suspected that the VOPO$_4$.2H$_2$O observed in the catalyst of FIG. 9 results from hydration of this Phase-X upon exposure of the catalyst to the atmosphere.

Figure 14:
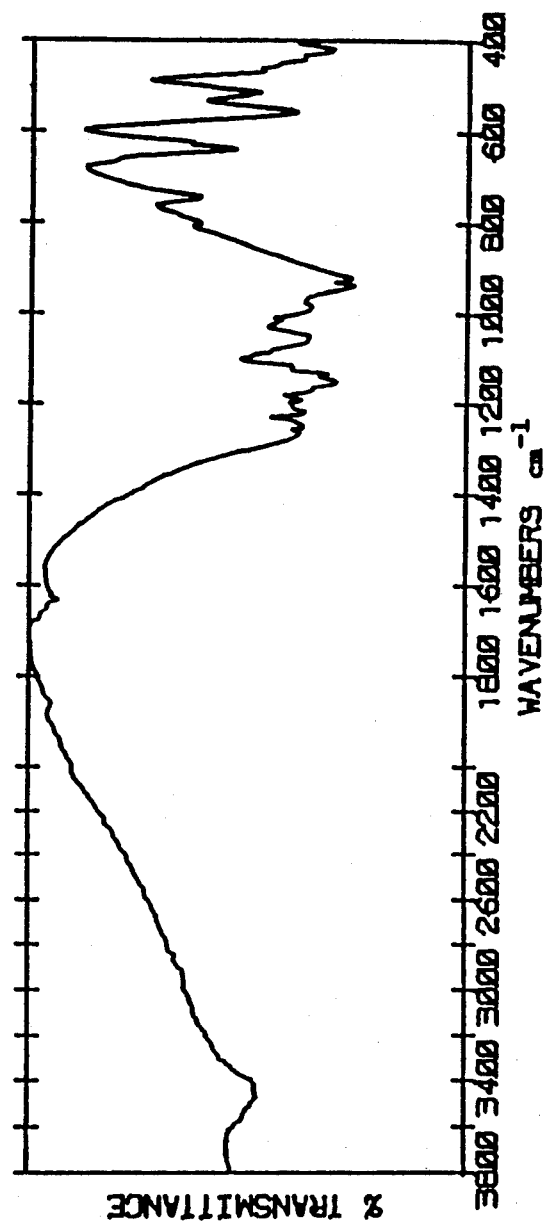
FIG. 14 is a mid-infrared spectrum of pure B-Phase produced as described herein.

Comparing the spectra of Phase-Z with that of FIG. 10 it can be seen that they are also quite different and additional peaks appear in the latter at 1260; 1189; 1130; 942; and 925 cm$^{-1}$. Referring to Table D and FIG. 14 described hereinafter, it can be seen that these peaks coincide with many of the I.R. peaks possessed by the pure B-Phase standard. When the catalyst of FIG. 10 is tested by x-ray diffraction analysis it is found to possess 15.2% B-Phase. Thus, it appears that for this catalyst, the I.R. spectra of FIG. 10 is of the type discussed above, wherein the catalyst possesses a sufficiently high proportion of B-Phase that some of its characteristic I.R. peaks have become visible. The remainder of the characteristic I.R. peaks of pure B-Phase reported in Table D are not observed, it is believed, because of spectral interferences caused by the remainder of the catalyst. The high B-Phase content of the catalyst of FIG. 10 and associated low yield of 35%, again support the conclusion that too much B-Phase will significantly reduce the yield of the catalyst. It is emphasized, that the conclusion that the non-common peaks of FIG. 10 are attributable to B-Phase is a reasonable one. However, it is also emphasized that whatever the cause of these non-common peaks, their appearance clearly renders the FIG. 10 catalyst different from that of the present invention.

Thus, it is concluded from the above data that the catalysts of the present invention possess a proportionally greater amount of at least one phase, i.e. Phase-Z (believed to be an amorphous phase) which possesses a higher activity than other phases known to be associated with prior art catalysts. While low yielding catalysts may also possess Phase-Z, it is believed that the proportional amount of Phase-Z in these catalysts can be diluted by the formation of less active phases or species (i.e. P-H bond containing species) particularly less active crystal phases (e.g. B-Phase), upon activation.

Accordingly, it is preferred that the catalysts of the present invention described herein possess a B-Phase content of typically not greater than about 10, preferably not greater than about 7, and most preferably not greater than about 4%; typically from about 0 to about 10, preferably from about 2 to about 7, and most preferably from about 2 to about 5%.

It has also been found that substantially no Phase-X (see U.S. Pat. No. 4,029,423) is present in the activated catalyst of the present invention, e.g., not greater than about 2%, preferably not greater than about 1%, and most preferably not greater than about 0%, as determined by x-ray diffraction spectrum data disclosed in U.S. Pat. No. 4,029,423. The absence of Phase-X is believed to be attributable to the absence of a strong acid treatment in the preparation of the catalysts of the present invention.

The water treatment step in conjunction with the activation procedure in a non-oxidizing atmosphere is believed to suppress the aforedescribed dilution effect by less active phases or species, possibly by disrupting or altering the surface arrangement of the vanadium, phosphorus and oxygen atoms thereby enhancing the formation of what is believed to be a more active amorphous phase.

The following are additional properties possessed by the fresh and/or activated catalysts of the present invention.

The fresh catalyst possesses a P:V atomic ratio of typically from about 0.5:1 to about 2:1, preferably from about 0.9:1 to about 1.5:1 and most preferably from about 1:1 to about 1.3:1.

The fresh catalyst also possesses an average vanadium valence of from about 3.9 to about 4.7, preferably from about 3.9 to about 4.4, and most preferably from about 3.9 to about 4.2 (e.g. 4.0).

The average phosphorus valence of the fresh catalyst typically will vary from about 3 to about 7, typically from about 4 to about 6 (e.g. 5).

The surface area of the fresh catalyst typically may vary from about 1 to about 30, preferably from about 3 to about 20, and most preferably from about 5 to about 15 m$^2$/g.

Upon activation in a non-oxidizing atmosphere, an as of yet unidentified crystalline phase (not B-Phase) is converted to a predominantly amorphous phase.

The P:V atomic ratio of the activated catalyst usually will decrease slightly upon activation and use relative to the fresh catalyst and in some instances may actually increase. Accordingly, the P:V atomic ratio of the activated catalyst typically can vary from about 0.9:1 to about 1.6:1, preferably from about 1:1 to about 1.4:1, and most preferably from about 1:1 to about 1.2:1 (e.g. 1:1 to 1.13:1).

The average vanadium valence of the activated catalyst can vary typically from about 3.9 to about 4.7, preferably from about 3.9 to about 4.4, and most preferably from about 3.9 to about 4.2 (e.g. 4.0).

The surface area of the activated unsupported catalyst can vary typically from about 10 to about 100, preferably from about 10 to about 50, and most preferably from about 10 to about 40 m$^2$/g.

The porosity of the activated catalyst can vary typically from about 10 to about 100.

The above properties are determined by the following analytical methods.

The average vanadium valence is determined from magnetic susceptibility measurements performed from 77° to 300° K. using the Faraday technique. Contributions due to ferromagnetic impurities are removed prior to evaluation of the data. The measurements are carried out in an applied field of 6.35 kG. The average vanadium valence is determined from the Curie constant determined from plots of inverse susceptibility versus temperature, as are the Weiss temperatures, .

Phosphorus to vanadium atomic ratio is determined by elemental analysis wherein vanadium is quantified by atomic absorption spectroscopy following acid digestion of the catalyst; quantification of phosphorus is conducted by gravimetric analysis using precipitation as the phosphomolybdate.

Surface area is determined by the BET method, the general procedures and theory for which are disclosed in H. Brunaur, P. Emmett, and E. Teller, J. of Am. Chem. Soc. Vol. 60, p. 309 (1938).

The presence or absence of X-Phase is determined by x-ray diffraction analysis based on the x-ray spectrum described in U.S. Pat. No. 4,209,423.

Porosity is determined by measuring the mercury pore volume at 16,000 psi and the apparent density at 16,000 psi and calculating the percent porosity from the equation:

% porosity = (Hg pore volume cc/g)(Apparent Density cc/g)100

The term "B-Phase", is defined herein to be a completely crystalline material possessing the empirical formula $(VO)_2P_2O_7$. Because limits on the amount of (i.e. %) B-Phase present in the catalysts of the present invention are believed to be important, an attempt has been made to synthesize as pure a form of B-Phase as possible to act as a standard in measuring the % B-Phase in these catalysts. The presence or absence of B-Phase is determined by x-ray diffraction analysis.

One route for preparing $(VO)_2P_2O_7$ is to first prepare $\beta$-$VOPO_4$ as an intermediate and convert this material under elevated temperature to the former. The overall reaction can be summarized as follows:

1. $V_2O_5 + H_2O + \underset{\underset{COOH}{|}}{COOH} + 2PO_4H_2NH_4 \longrightarrow$ $(NH_4)_2 [(VO)_2C_2O_4(HPO_4)] \cdot 5H_2O$ (green)

2. $(NH_4)_2 [(VO)_2C_2O_4(HPO_4)] \cdot 5H_2O \longrightarrow \beta\text{-}VOPO_4$ (yellow)

3. $\beta\text{-}VOPO_4 \longrightarrow (VO)_2P_2O_7$ (gray)

Example 15 provides a more detailed description of the preparation of $(VO)_2P_2O_7$.

The characteristic x-ray diffraction spectrum of what is believed to be pure $(VO_2)P_2O_7$ is reported in Table C. The actual x-ray diffraction spectrum is provided at FIG. 13.

TABLE C

| d (Angstrom) | Line Position 2 ⊖ Degrees | Intensity %* |
|---|---|---|
| 3.8651 | 23.01 | VS-S |
| 3.1323** | 28.49 | VS |
| 2.9795 | 29.99 | M |
| 2.6545 | 33.76 | VW-W |
| 2.4359 | 36.90 | VW-W |
| 2.0909 | 43.27 | W |
| 2.0847 | 43.40 | VW |
| 1.9337 | 46.99 | VW |
| 1.8391 | 49.57 | VW |
| 1.6351 | 56.26 | VW |
| 1.5760 | 58.57 | W |
| 1.5715 | 58.76 | VW |
| 1.4729 | 63.12 | VW |
| 1.4596 | 63.76 | VW |

*See Table B for definition of intensity symbols
**Used for normalization

The characteristic mid-infrared spectra of pure $(VO)_2P_2O_7$ are summarized at Table D. The actual mid-infrared spectrum is provided at FIG. 14.

TABLE D

| Cm$^{-1}$ | Intensity* |
|---|---|
| 1263 | S |
| 1248 | S |
| 1217 | S |
| 1202 | S |
| 1188 | S |
| 1165 | S |
| 1150 | VS |
| 1128 | VS |
| 1119 | S |
| 1113 | S |
| 1057 | S |
| 1049 | S |
| 1011 | S |
| 986 | S |
| 937** | VS |
| 918 | VS |
| 799 | W |
| 743 | W |
| 637 | M |
| 621 | W |
| 556 | S |
| 512 | M |
| 469 | M |
| 442 | S |
| 419 | VS |
| 401 | S |

Figure 13:
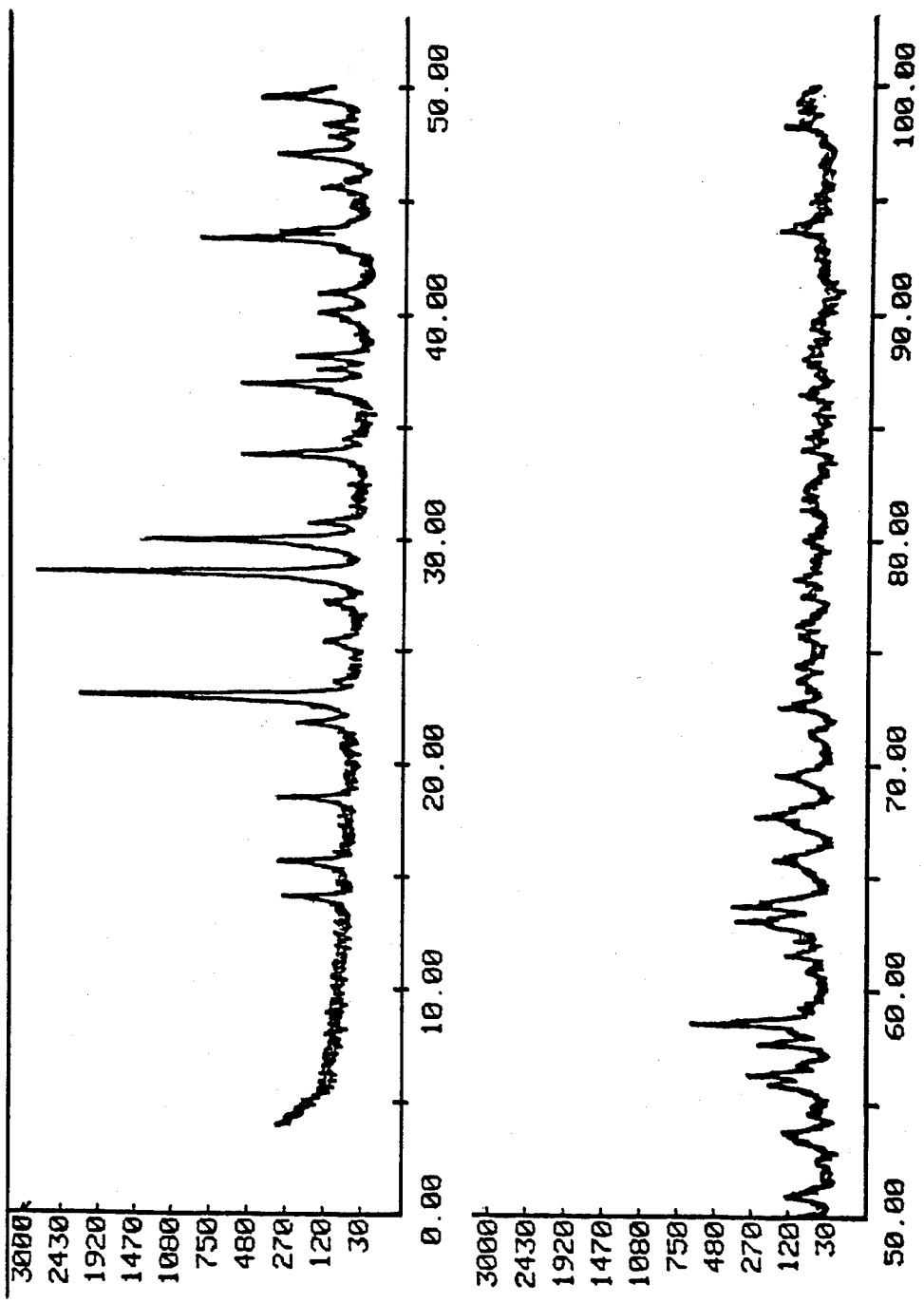
FIG. 13 is an x-ray diffraction spectrum of pure B-Phase produced as described herein.

*See Table B for definition of intensity symbols
**100% band used for normalization It is appropriate to point out that many more d-spacings are visible in FIG. 13 for pure $(VO_2)P_2O_7$ than are disclosed in Table C. The d-spacings reported in Table C are believed to characterize the strongest peaks of B-Phase, all of these peaks having an intensity of at least 10%. The justification for eliminating minor peaks from Table C is based on the observation that as the purity of the B-Phase is diminished by the presence of non-B-Phase material, many of the characteristic minor peaks of B-Phase may be lost due to spectral interference. Consequently, the presence or absence of B-Phase is determined herein by the presence of at least the 7 highest peaks of those reported in Table C. The % B-Phase is also determined in the absence of any promoters, stability agents; or attrition assistant modifiers, or supports described herein.

The % B-Phase in a catalyst sample and as reported herein is determined using x-ray diffraction data from the catalyst sample and pure B-Phase standard as follows. An x-ray diffraction spectrum of the catalyst sample as received is obtained using a Phillips Automatic Powder Diffractometer.

The sample is then mixed with alpha alumina in a 5:1 ratio and an x-ray diffraction scan collected using identical scanning parameters employed for catalyst alone. The ratio of intensities of the 3.9 Å peak of the sample to that of the 2.085 Å peak of the alpha alumina standard is a measure of the relative amount of $(VO)_2P_2O_7$ contained in the catalyst.

A correction factor is obtained if the intensity of the sample peak is less than the intensity of the sample plus the internal standard at 3.9 Å. In some cases, the catalyst sample also shows a peak at 2.085 Å. The correction factor is applied to the sample contribution at 2.085 Å and the product obtained is then subtracted from the measured intensity of the alpha alumina standard peak. A ratio of the corrected values of the 3.9 Å intensity due to the catalyst and the 2.085 Å intensity due only to the internal standard is then determined.

The pure B-Phase standard is also analyzed in the manner described above and its intensity ratio is 44:1. This ratio is considered to represent 100% $(VO)_2P_2O_7$ (B-Phase) and is used to calculate the % B-Phase present in any V-P-O type catalyst sample.

The scanning parameters for the x-ray diffraction analysis are as follows:

| Wattage | 45 KV |
| --- | --- |
|  | 40 milliamps |
| Slits | Variable diverging slit |
|  | .25° receiving slit |
| Radiation | CuKα λ = 1.5418 |
| Scan Rate | 2°/min. |
| Range Scanned | 4–100° 2 ⊖ |

VII. Vapor Phase Oxidation of Hydrocarbons

A. The catalysts of the present invention can be used to at least partially oxidize hydrocarbons to their corresponding carboxylic anhydrides. Such hydrocarbons which can be utilized in conjunction with the catalysts described herein comprise alkanes, typically alkanes of from 4 to about 10, preferably from about 4 to about 8, most preferably from about 4 to about 6 carbons; alkenes, typically alkenes of from about 4 to about 10, preferably from about 4 to about 8, most preferably from about 4 to about 6 carbons; cycloalkanes or cycloalkenes, typically cycloalkanes or cycloalkenes of from about 4 to about 14, preferably from about 6 to about 12, and most preferably from about 6 to about 10 carbons; alkyl substituted and unsubstituted aromatic compounds wherein the aryl portion thereof contains typically from about 6 to 14, preferably from about 6 to about 10 (e.g., 6) carbons and the alkyl portion contains typically from about 1 to about 10, preferably from about 1 to about 5 carbons, and mixtures thereof.

Representative examples of suitable alkanes include butane, pentane, isopentane, hexane, 3-methyl pentane, heptane, octane, isooctane, decane and mixtures thereof.

Representative examples of suitable alkenes include butene-1, butene-2 (cis or trans), 3-methylbutene-1, pentene-1, pentene-2, hexene-1, 3,3-dimethylbutene-1, 3-methylpentene-2, butadiene, pentadiene, cyclopentadiene, hexadiene, and mixtures thereof. It is also contemplated to use refinery streams rich in alkenes, particularly streams containing 70 percent or more butenes.

Representative examples of cycloalkanes, which can be methyl substituted, include cyclobutane, cyclopentane, methylcyclopentane, cyclohexane, methylcyclohexane, 1,4-dimethylcyclohexane, cycloheptane, and cyclooctane. Mixtures of hydrocarbons rich in alkanes and cycloalkanes having between 4 and 10 carbon atoms, i.e., containing about 70 weight percent or more alkanes and cycloalkanes can also be used.

Representative examples of suitable aromatic compounds include benzene, toluene, xylene, cumene, pseudocumene, durene and mixtures thereof.

Heterocyclic compounds such as furan, benzofuran, thiophene can be employed. Also suitable and readily available are naphthas obtained from paraffinic or naphthenic petroleum sources. Full boiling range naphthas (boiling within the range of about 35°–230° C.) can be used but it is preferred to use light naphtha cuts boiling within the range of about 35°–145° C. The naphthas usually contain about 5–15 percent benzene and alkylbenzenes. It will be understood that other mixtures can be used, such as a paraffinic raffinate from the glycol-water solvent extraction of reformates.

Thus, the catalyst of the present invention can be used to convert butane or butene to maleic anhydride; isopentane or isopentene to citraconic anhydride, maleic anhydride and α-carboxy maleic anhydride; pseudocumene to trimellitic anhydride; durene to pyromellitic anhydride; and o-xylene to phthalic anhydride.

A preferred hydrocarbon feed for the catalyst of the present invention for conversion to maleic anhydride is a n-$C_4$ hydrocarbon comprising a predominant amount of n-butane and more preferably at least 90 mol percent n-butane. In the following discussion and exemplification, therefore, butane is used in most examples to demonstrate (but not to limit) the use of the catalysts made by the process of this invention for producing maleic anhydride. It is contemplated that mixtures rich in butane can also be used, such as typical butane-butene refinery streams.

B. Preparation of Maleic Anhydride

The oxidation of n-butane to maleic anhydride may be accomplished by contacting n-butane, in low concentrations with oxygen in the presence of the described catalyst. Air is entirely satisfactory as a source of oxygen, but synthetic mixtures of oxygen and diluent gases, such as nitrogen, carbon dioxide and the like also may be employed. Air enriched with oxygen may be employed.

The gaseous feed stream to the oxidation reactors normally will contain air and typically from about 0.5 to about 10, preferably from about 1 to about 8, and most preferably from about 1.2 to about 5 mole % butane. About 1.0 to about 1.9 mole % of the butane in air is satisfactory for optimum yield of product for the process of this invention using a fixed bed reactor, and from about 2.5 to 4.0 mole % butane using a fluidized bed. Although higher concentrations may be employed, explosive hazards may be encountered. Lower concentrations of butane less than about 1%, of course, will reduce the production rate obtained at equivalent flow rates and thus are not normally economically employed.

Flow rates of the gaseous feed stream typically will be sufficient to provide a contact time with the catalyst of from about 0.5 to about 5, preferably from about 0.5 to about 3.5, most preferably from about 0.5 to about 2.5 seconds. At contact times of less than about 0.5 seconds, less efficient operations are obtained.

A variety of reactors will be found to be useful and multiple tube heat exchanger type reactors are quite satisfactory. The tubes of such reactors may vary in diameter typically from about ¾ inch to about 2 inches, and the length may be varied from about 3 to about 15 feet.

The oxidation reaction is an exothermic reaction and, therefore, relatively close control of the reaction temperature should be maintained. It is desirable to have the surface of the reactors at a relatively constant temperature and some medium to conduct heat from the reactors is necessary to aid temperature control. Various heat conductive materials may be employed, but it has been found that eutectic salt baths are completely satisfactory. One such salt bath is described below and is a eutectic constant temperature mixture. As will be recognized by one skilled in the art, the heat exchange medium may be kept at the proper temperature by heat exchangers and the like. The reactor or reaction tubes may be stainless steel, carbon-steel, nickel, glass tubes such as Vycor and the like. Both carbon-steel and nickel tubes have excellent long life under the conditions of the reactions described herein.

Optionally, the reactors contain a preheat zone of an inert material such as ¼ inch Alundum pellets, inert ceramic balls, metallic balls or chips and the like, present at about ½ to 1/10 the volume of the active catalyst present.

The temperature of reaction may be varied within some limits, but normally the reaction should be conducted at temperatures within a rather critical range. The oxidation reaction is exothermic and once reaction is underway, the main purpose of the salt bath or other media is to conduct heat away from the walls of the reactor and control the reaction. Better operations are normally obtained when the reaction temperature employed is no greater than about 100° C. above the salt bath temperature. The temperature in the reactor, of course, will also depend to some extent upon the size of the reactor and the butane concentration. Under usual operating conditions, in compliance with the preferred procedure of this invention, the average bed temperature referred to herein as the reaction temperature, measured by thermocouples disposed in the reactor, is typically from about 350° to about 450°, preferably from about 360° to about 420°, and most preferably from about 370° to about 410° C. Described another way, in terms of salt bath reactors with reactor tubes about 1.5 inches in diameter, the exit salt bath temperature will typically be controlled from about 330° to about 430°, preferably from about 340° to about 400°, and most preferably from about 350° to about 390° C. Under normal conditions, the temperature in the reactor ordinarily should not be allowed to go above about 450° C. for extended lengths of time because of decreased yields and possible deactivation of the novel catalyst of this invention.

The reaction may be conducted at atmospheric, superatmospheric or below atmospheric pressure.

The maleic anhydride may be recovered by a number of ways well known to those skilled in the art. For example, the recovery may be by direct condensation or by absorption in suitable media, with subsequent separation and purification of the maleic anhydride.

While the above discussion is directed primarily to the use of a butane containing feed gas, it is equally applicable to the use of other hydrocarbon feed gases described herein subject to any modifications which would be obvious to one skilled in the art.

The following examples are given as specific illustrations of the claimed invention. It should be understood, however, that the invention is not limited to the specific details set forth in the examples. All parts and percentages in the examples as well as in the remainder of the specification are by weight unless otherwise specified.

In the following examples, two general types of reactors are employed. The results of the tests in the two reactors are qualitatively comparable, i.e., an increase in maleic anhydride yield in the smaller equipment will be reflected in the larger equipment, although the absolute numbers are different.

Reactor Type 1 is U-shaped with one arm as the preheater (empty) and the other arm for packing catalyst. The reactor tube for the catalyst bed has a ⅜" O.D., 0.305" I.D., and either 7 inches (Type 1A) or 10 inches (Type 1B) in length, and is made of a stainless steel tube. Five cc (Reactor Type 1A) or 8 cc (Reactor Type 1B) of catalyst is charged to the reactor for testing and a 1/16 inch outer diameter thermocouple is placed 1 inch from the inlet of the catalyst bed to measure the reaction temperature. The reactor tube is immersed in a salt bath having a composition as described for reactor Type 2. Reactor inlet pressure is about 1 psig. Once a catalyst evaluation is started, the reaction is continued without interruption until the end of a series of runs. Recoveries are made at convenient time intervals. During a recovery, a scrubber with deionized water is placed in an ice-water bath and is connected to the reactor effluent to trap maleic anhydride and other condensable products. The scrubber effluent is connected to an on-line gas chromatograph for tail gas analysis. Maleic anhydride is titrated as maleic acid along with other acids using a potentiometer. Carbon balance is calculated according to the number of g-atoms of carbon in the reactor effluent to the g-atoms of carbon fed to the system. Nitrogen balance (in the air) is also calculated according to the g-moles of nitrogen found in the reactor effluent to the g-moles of nitrogen fed to the system.

Reactor Type 2 consists of a single straight stainless steel tube I.D. 19 mm, O.D. 28 mm, and length of 4000 mm. This stainless steel tube, which contains the catalyst and is referred to as the catalyst tube, is inserted into a larger stainless steel tube, referred to herein as the salt bath tube, with dimensions of I.D. 100 mm, O.D. 108 mm, and length of 4000 mm. The salt bath tube is equipped with a nitrogen purge line that extends to the bottom thereof through which flows nitrogen gas to stir the salt bath and provide uniform heating. The salt bath tube is filled with HITEC ® salt during operation. The salt bath tube is closed-off from the catalyst tube. The salt bath tube is wrapped with a 13.5 kw heating coil. Wrapped around the heating coil is low heat conductive insulation having a thickness of 110 mm. The entire assembly is then inserted into an outer steel tube. The catalyst tube is equipped with 24 Type J thermocouples which are spaced along the center thereof. Likewise, the salt bath tube is equipped with 6 Type J thermocouples evenly spaced along the length thereof. 3000 mm of the catalyst tube is filled with catalyst pellets. The components of the feed gas are separately metered into a common line which enters the top of the catalyst tube. A gaseous mixture containing product is collected from the bottom of the catalyst tube and passed through a cold water trap which condenses most of the maleic anhydride product. This condensate is analyzed by potentiometric titration and the remaining gaseous components analyzed by gas phase chromatography. The reaction temperature, as reported herein, is determined from an average of the catalyst tube thermocouple readings. Likewise for the salt bath temperature.

Conversion of butane is calculated according to the following equation:

$$\% \text{ butane conversion} = \frac{\text{g moles of reacted butane}}{\text{g moles of butane fed}} \times 100$$

Maleic anhydride yield is calculated according to the following equation:

$$\% \text{ MA yield} = \frac{\text{g mole of maleic anhydride produced}}{\text{g moles of butane}} \times 100$$

The selectivity of maleic anhydride is calculated according to the following equation:

$$\% \text{ selectivity to MA} = \frac{\text{g moles of maleic anhydride produced}}{\text{g moles of butane reacted}} \times 100$$

Unless otherwise specified, all of the catalysts prepared in accordance with the following examples of the present invention possess a P:V atomic ratio of between 1:1 and 1.2:1, an average vanadium valence of 3.9 to 4.1, and a surface area of 5 to 15 m²/g. Furthermore, all preparations of the first catalyst precursor are conducted using azeotropic distillation to remove water and other low boiling components formed in-situ.

EXAMPLE 1

23.6 g of $V_2O_5$, 30.6 g of 100% orthophosphoric acid, and 500 cc of isobutanol are stirred, heated and refluxed together for 24 hours (a blue color slurry is obtained) while removing water formed in-situ by azeotropic distillation. The slurry is filtered, and the recovered filter cake heated in an oven at 145° C. to dryness (1.5 hour) to form the first catalyst precursor. Forty-seven grams of the first catalyst precursor are then slurried with 430 g of water and the slurry heated and evaporated at about 80° C. for about 4 hours to form a wet paste. The paste is then dried in a hot air oven at 125° for 1 hour. The fresh catalyst is then sized to −10 to +20 mesh (Tyler series) and 5 cc thereof placed in the Type 1A reactor. The fresh catalyst is then activated in-situ by passing a 1.2 mole % gaseous mixture of n-butane in air at 400° C. over the catalyst at a contact time of 3 sec. for a period of 5 hours. The temperature is then lowered to 390° C. at a contact time of 2.5 sec. At 74.5 hours on stream time the yield is 64.1% and the selectivity is 65.9% and the catalyst is considered activated. The reaction is then allowed to run for a total on stream time of 2950 hours including activation. After 2864 on stream time the temperature is lowered to 380° C., and then to 375° C. after 2920 hours on stream time to compensate for an increase in catalyst activity. Samples are tested at various on stream times and the results summarized at Table 1.

TABLE 1

| Reaction Temp. (°C.) | Hours on Stream | Maleic Anhydride Yield % | Butane Conversion % | Selectivity % |
|---|---|---|---|---|
| 390 | 74.5 | 64.1 | 97.5 | 65.9 |
| 390 | 577 | 64.8 | 91.3 | 71.0 |

TABLE 1-continued

| Reaction Temp. (°C.) | Hours on Stream | Maleic Anhydride Yield % | Butane Conversion % | Selectivity % |
|---|---|---|---|---|
| 390 | 647 | 64.2 | 88.7 | 72.4 |
| 390 | 1081 | 64.7 | 90.9 | 71.1 |
| 390 | 1181 | 66.0 | 92.5 | 71.4 |
| 390 | 1272 | 64.7 | 89.9 | 71.9 |
| 390 | 1637 | 66.2 | 95.7 | 69.2 |
| 390 | 2117 | 64.2 | 95.9 | 67.0 |
| 375 | 2934 | 64.0 | 90.6 | 70.7 |

EXAMPLE 2

This example illustrates an embodiment of the invention wherein the water contacting the first catalyst precursor is steam.

The catalyst material is prepared the same as in Example 1. After the paste material is dried in an oven, as described, 3.75 g of the material are molded to 5 cc, ⅜″ diameter pellets using 0.25 g of binder containing 70% Sterotex ® and 30% graphite. The pellets are packed in a tube and purged with a stream of steam at 150° C., for 5 hours. The material is then further dried at 120° C. for 2 hours. The material is then sized to −10 to +20 mesh (Tyler Series) and activated in-situ as described in Example 1. Similar results as Example 1 are expected.

EXAMPLE 3

In a reflux flask, 36.4 g of $V_2O_5$ is suspended in 350 cc isobutanol. 47.0 g of 100% orthophosphoric acid dissolved in 150 cc isobutanol is added to the flask. The solution-suspension is heated, stirred, refluxed overnight, and filtered. The cake material is dried in an oven at 140° C. to dryness for 1.5 hours to form the first catalyst precursor.

A separate aqueous V/P oxide solution is also prepared by admixing in a prepared beaker 3.64 g of $V_2O_5$ and 9.1 g of oxalic acid in 400 cc of water. The mixture is stirred and heated to obtain a clear blue color solution. 5.53 g of 85% $H_3PO_4$ is then added to the solution which is then stirred and heated at temperature reflux overnight (i.e., 18 hours). The solution is then cooled to about 40° C.

All of the first catalyst precursor, as described above, is then mixed with all of the cooled solution. The mixture is then stirred and heated at about 80° C. for about 5 hours, evaporated to thick slurry, and dried in an oven at 120° C. overnight (18 hours). The fresh catalyst material is sized to −10 +20 mesh (Tyler Series) and activated in-situ as described in Example 1 for 68 hours at 400° C. (contact time 2.5 sec.). The feed gas is allowed to flow (contact time 2.5 sec.) for a total of 861 hours and analyzing the product periodically. The results are summarized at Table 2.

TABLE 2

| Temp. °C. | Hours on Stream | Maleic Anhydride (M.A.) Yield % | Butane Conversion % | Selectivity % |
|---|---|---|---|---|
| 400 | 68 | 43.6 | 73.3 | 59.5 |
| 400 | 432 | 50.5 | 74.9 | 67.4 |
| 400 | 764 | 60.6 | 90.7 | 66.8 |
| 400 | 861 | 62.4 | 88.7 | 70.3 |

Comparative Example 1

This example illustrates the products realized from an organic solution reduction method in the absence of a water treatment step.

A catalyst prepared according to the general organic solution reduction method using HCl as a reducing agent described (col. 2, line 15 to col. 3, line 2) in U.S. Pat. No. 3,864,280 with 45.5 g of $V_2O_5$, 58.8 g of crystalline orthophosphoric acid and 310 cc of isobutanol. The resulting material is dried in an oven at 135° C. for 1.75 hours, sieved as in Example 1, and then activated in-situ in reactor Type 1A, under reaction conditions of 400° C. with 1.2 mole % n-butane in air feed (contact time 2 sec.) Note that the hours on stream of Table 3 include activation. The yield results are summarized at Table 3, Contact time during reaction is 2 sec. and feed gas is 1.2 mole % n-butane in air.

TABLE 3

| Temp. °C. | Hours on Stream | Maleic Anhydride (M.A.) Yield % | Butane Conversion % | Selectivity % |
|---|---|---|---|---|
| 400 | 4 | 10.7 | 25.9 | 41.2 |
| 400 | 29 | 14.8 | 32.8 | 45.0 |
| 400 | 217 | 28.6 | 45.8 | 62.4 |
| 400 | 313 | 33.8 | 50.9 | 66.5 |
| 400 | 485 | 33.9 | 51.0 | 66.4 |

Comparative Example 2

The procedure of Comparative Example 1 is followed however, no HCl is added to solubilize the vanadium compound.

Thus, in a reflux flask, 36.4 g of $V_2O_5$ is suspended in 300 cc isobutanol. 47.0 g of crystalline orthophosphoric acid dissolved in 200 cc of isobutanol is then added. The mixture is heated, stirred, and refluxed overnight (i.e., 18 hours). One hundred cc of liquid organic media is removed by distillation. The resulting slurry is evaporated to a thick paste using a steam bath and the resulting paste dried in an oven at 150° C. to dryness. The dried material is then heated in a forced hot air tube furnace at 400° C. for two hours in air, sized to −10 +20 mesh (Tyler Series), heated again in-situ in a Type 1A reactor under the same activation conditions of temperature, contact time, feed and feed flow as Comparative Example 1 and these conditions maintained during the course of the reaction.

The results are summarized at Table 4.

TABLE 4

| Temp. °C. | Hours on Stream | Maleic Anhydride (M.A.) Yield % | Butane Conversion % | Selectivity % |
|---|---|---|---|---|
| 400 | 22.5 | 10.5 | 24.0 | 43.6 |
| 400 | 338 | 29.2 | 51.0 | 57.1 |
| 400 | 507 | 49.7 | 91.2 | 55.1 |

Comparative Example 3

This example illustrates the performance of a catalyst prepared generally in accordance with Katsumoto et al U.S. Pat. No. 4,132,670.

Thus, a catalyst is prepared by the procedure of Example 1 of the '670 patent as follows. A reflux flask is charged with 182 parts by weight $V_2O_5$ and 656 parts by weight of isobutanol. The contents are refluxed for 3 hours, removing water by azeotropic distillation. Then, 277 parts by weight of 85% phosphoric acid is added slowly and the reaction temperature maintained at reflux for an additional 6 hours, removing water as formed. After standing at room temperature for 60 hours, the reaction mixture is heated at reflux for 7 hours removing water as formed. After standing for 20 hours at room temperature, the solvent is removed by distillation to form the slurry to leave 413 parts by weight of a blue solid which is ground to less than 20 mesh (Tyler Series). To 150 parts by weight of this powder is added 35 parts by weight of water. The resulting paste is used to form tablets 1.2 mm in diameter (extrusion equipment being unavailable). The tablets are then dried in a forced hot air oven at 150° C. for 2 hours. The dried tablets are then placed in the Type 1A reactor and heated in a stream of air at 380° C. for 2 hours. The temperature of the air stream is slowly raised to 480° C. over 1 hour during which time 1.4 mole % n-butane is introduced into the air stream (contact time 2.4 sec.). Heating is continued at 480° C. for about 15 hours. The temperature of the reactor is then lowered to 442° C. and a sample of product analyzed after 216 hours and 384 hours at 442° C. The maleic anhydride yield is 46%, conversion is 100%, and selectivity is 46% after 216 hours and after 384 hours yield is 47%, conversion is 100%, and selectivity is 47%. The catalyst after 384 hours is tested as described in Example 16 and the results summarized at Table A. cl Comparative Example 3A Comparative Example 3 is repeated with the exception that the fresh catalyst is activated in a 1.2 mole % n-butane air stream mixture at 390° C. for 48 hours (contact time 2.5 sec.). At this point the reaction temperature is controlled to be 390° C. and the reaction continued for 192 hours (contact time 2.5 sec.) at this temperature. Product is analyzed and the maleic anhydride yield is 51.0%, conversion is 88%, and selectivity is 58%.

Selected results from Examples 1 and 3, and Comparative Examples 1, 2, 3 and 3A are summarized at Table 4A.

It can be seen from the data of Table 4A that whether the organic preparative method employs HCl or not to reduce the vanadium, in the absence of hot water treatment step, the maleic anhydride yields are significantly reduced.

Furthermore, it can also be seen that the mere use of water to form a paste of the unactivated catalyst does not constitute nor produce the results of the hot water treatment step of the present invention since the proper combination of water temperature and contact time is absent. This applies whether activation is conducted in air alone followed by air-butane or by an air-butane mixture in the absence in air alone. Note also the reduction in yield associated with activation in air followed by air and butane relative to an air-butane mixture in the absence of air alone.

TABLE 4A

| Example | Preparation Type | Hours on Stream | Reaction Temp. °C. | M.A. Yield % | Butane Conversion % | Selectivity % |
|---|---|---|---|---|---|---|

TABLE 4A-continued

| No. | Preparation Type | Hours on Stream | Reaction Temp. °C. | M.A. Yield % | Butane Conversion % | Selectivity % |
|---|---|---|---|---|---|---|
| 1 | Organic without HCl, with hot water treatment | 74.5<br>577 | 390<br>390 | 64.1<br>64.8 | 97.5<br>92.5 | 65.9<br>71.4 |
| 3 | Organic without HCl, with modified hot water treatment (water contains dissolved V/P/O) | 432<br>861 | 400<br>400 | 50.5<br>62.4 | 74.9<br>88.7 | 67.4<br>70.3 |
| Comparative Example No. | | | | | | |
| 1 | Organic with HCl, without hot water treatment | 482 | 400 | 33.9 | 51.0 | 66.4 |
| 2 | Organic, without HCl, without hot water treatment | 507 | 400 | 49.7 | 91.2 | 55.1 |
| 3 | Organic without HCl, with water paste forming step but without hot water step, activation in air and then air and butane. | 216 | 442 | 45.5 | 100 | 46 |
| 3A | Organic, without HCl, with water paste forming step, without hot water step, activation in air-butane mixture. | 192 | 390 | 51.0 | 88.0 | 58.0 |

The following Example 4 of the present invention and Comparative Example 4 illustrate the effect of omitting the water treatment step in the embodiment wherein $V_2O_5$ is separately contacted and heated in isobutanol before the addition of the orthophosphoric acid.

EXAMPLE 4

A reflux flask is charged with 45.5 g $V_2O_5$ and 600 ml of isobutanol. The slurried contents are refluxed for 3 hours at 105° C. removing water by azeotropic distillation. Then, 61.2 g of crystalline orthophosphoric acid, dissolved in 300 ml of isobutanol is added to the flask and the reaction temperature maintained at reflux (105°C.) for an additional 20 hours, removing water as formed. The slurry is then filtered and dried as described in Example 1. Then, 20 parts by weight of the first catalyst precursor are slurried with 100 parts by weight water and the mixture heated and evaporated at 80° C. for 2 hours to form a paste. The paste is then dried in a forced hot air oven at 140° C. for 2 hours. The fresh catalyst is then sized as in Example 1, placed in a Type 1A reactor, and activated by passing a 1.2 mole % n-butane in air mixture for 120 hours through the reactor at contact time of 2 sec. The activation temperature is 390° C. Upon completion of activation the reaction temperature is lowered to 385° C. The air-butane mixture continues to pass through the reactor at a contact time of 2.4 sec. for 312 hours (measured from the beginning of activation) at which time a sample of product is analyzed. The results are summarized at Table 5.

Comparative Example 4

A catalyst is prepared in accordance with Example 4 with the exception that the water treatment step is omitted. Thus, the dried first catalyst precursor is sized in accordance with Example 4 and activated in a 1.2 mole % n-butane-air mixture at 390° C. for 120 hours (contact time 2.2 sec).

Upon completion of the activation, the reaction temperature is maintained at 390° and the reaction terminated after 272 hours (including activation time). The contact time during reaction is 2.3 sec. Product analysis is conducted and the results summarized at Table 5.

The following Example 5 of the present invention and Comparative Example 5 illustrate the embodiment wherein reduction and reaction of the $V_2O_5$ (with the phosphorus compound) occur in the presence of orthophosphoric acid and shows the effect of omitting the water treatment step in this embodiment.

EXAMPLE 5

The fresh catalyst is prepared in accordance with the procedures of Example 4 with the following exceptions: The following amounts of ingredients are employed: 1090 g $V_2O_5$; 1411 g 100% orthophosphoric acid, 9600 g isobutanol, refluxed for 27 hours at 103°–104° C.; filter cake heated 2 hours at 125° C.; 2165 g first catalyst precursor slurried with 14,000 g of water; slurry evaporated for 14 hours at 80°–90° C. to form a thick paste; paste dried in oven at 120° C. for 8 hours. However, a portion of the first catalyst precursor prior to water treatment is set aside for use in Comparative Example 5.

The fresh catalyst is then placed in the type 1B reactor and activated in a 1.1 mole % mixture of n-butane in air-stream (contact time 2.0 sec.) at a temperature of 400° C. for 25 hours. At this point the temperature is gradually lowered to 375° C. and the reaction allowed to proceed for 212 hours (including activation), contact time being 2.0 sec. during reaction. Product samples are removed, analyzed, and the results shown at Table 5. The above procedure is repeated twice and product analyzed after 220 hours and 240 hours. Each catalyst sample is also analyzed in accordance with the procedures of Example 16 and the results summarized at Table A.

Comparative Example 5

Using the first catalyst precursor set aside in Example 5 and in the absence of a water treatment step, the first catalyst precursor is sized in accordance with Example 1, placed into a Type 1B reactor. It is therein activated in a 1.1 mole % n-butane air-stream (contact time 2.0 sec.) at 400° C. for 25 hours. The reaction temperature is lowered to 380° C., contact time is 2.2 sec., and the reaction allowed to proceed for 192 hours including activation time. Product samples are analyzed, and the results summarized at Table 5.

The following Examples 6 and 7 of the present invention illustrate the significant improvement in yield achieved by activation of the fresh catalyst in a nonoxidizing atmosphere only, rather than air alone and then air and butane.

EXAMPLE 6

A fresh catalyst is prepared in accordance with the procedures of Example 1 with the exception that pellets are made with 5% Sterotex ® and 2% graphite and the pellets crushed and sieved to −10 +20 mesh (Tyler Series). The sized fresh catalyst is then divided into two portions, one for use in Example 6 and the other for use in Example 7. The first portion is placed in a Type 1A reactor and activated in a 1.2 mole % n-butane-air stream at 400° C. for 21 hours (contact time 2.9 sec.). The reaction temperature is then lowered to 390° C., contact time 2.5 sec., and the reaction allowed to proceed for 360 hours (including activation). At this point product is analyzed, and the results are summarized at Table 5. The reaction allowed to continue to 506 hours on stream and then tested as in Example 16, the results being summarized at Table A.

EXAMPLE 7

The second portion of sized fresh catalyst from Example 6 is placed in a forced hot air oven and heated to 400° C. for 2 hours. The sample is then placed in a Type 1A reactor and contacted with a 1.2 mole % n-butane in air stream at 400° C., a contact time of 2.6 seconds, and for a period of 168 hours. At this point product is analyzed and the results summarized at Table 5.

comparing the results of Example 5 with Example 4 it can be seen that a significant improvement in yield is obtained using the simultaneous reduction/reaction embodiment versus the separate $V_2O_5$ treatment embodiment.

Comparing the results of Examples 6 and 7, it can be seen that activation in air alone and then in an air-butane mixture, significantly reduces the yield of the reaction. It is for this reason that activation in a non-oxidizing atmosphere is preferred.

EXAMPLE 8

This example demonstrates the unique ability of the catalyst of the present invention to achieve rapid activation. A catalyst is prepared according to the catalyst preparation procedure described for Example 1 and designated 8-1. For comparison, an organic based catalyst preparative method without HCl and without water treatment is prepared according to the catalyst procedure used for Comparative Example 2 and is designated 8-2.

The reaction system, feed conditions and method used for analysis are similar to the one described for Example 1.

Product effluent stream for each system is analyzed as a function of time for maleic anhydride selectivity and yield. The data obtained is reported in Table 6. The data clearly show that while the catalyst of the present invention equilibrates in about 80 hours to give a yield of about 63% at 93.6% conversion, the second catalyst system based on organic preparation without HCl having no post-water treatment needs, almost 500 hours to

TABLE 5

| Example No. | Mole % n-Butane in Air-Butane Mixture | Reaction Temp. °C. | Contact Time During Reaction Sec. | Hours on Stream | M.A. Yield % | Butane Conversion % | Selectivity % | Comments |
| --- | --- | --- | --- | --- | --- | --- | --- | --- |
| 4 | 1.1 | 385 | 2.4 | 312 | 60.2 | 91 | 66 | Separate $V_2O_5$— isobutanol treatment embodiment. |
| 5 | 1.1 | 375 | 2.0 | 212 | 65.5 | 91.5 | 71.6 | Simultaneous $V_2O_5$ reduction and reaction. |
| 6 | 1.2 | 390 | 2.5 | 360 | 64.0 | 90.5 | 71.0 | Activation in n-butane-air mixture only. |
| 7 | 1.2 | 400 | 2.6 | 168 | 56.7 | 89.7 | 63.2 | Activated in air only at 400° C. for 2 hrs. and then in air-butane mixture. |
| Comparative Example No. | | | | | | | | |
| 4 | 1.3 | 390 | 2.3 | 272 | 54.2 | 81.4 | 59.3 | Omits water treatment step. Compare with Ex. 4. |
| 5 | 1.1 | 380 | 2.2 | 192 | 43.4 | 71.5 | 60.9 | Omits water treatment step. Compare with Ex. 5. |

As may be seen from the data of Table 5, the criticality of the water treatment step is established for both the separate $V_2O_5$ treatment embodiment and the simultaneous $V_2O_5$ reduction and reaction embodiment. Also, achieve steady state conditions wherein the yield at which conversion is stabilized is significantly below 63% (i.e., 49.7%).

TABLE 6
CATALYST ACTIVATION COMPARISON FOR BUTANE OXIDATION TO MALEIC ANHYDRIDE

| Example | Catalyst | Preparation | Activation | Mole %* n-butane in Air-Butane Feed Stream | Reaction Temp. °C. | Hours On Stream | M.A. Yield % | Butane Conversion % | Selectivity % |
|---|---|---|---|---|---|---|---|---|---|
| 8-1 | V/P/O | Organic without HCl but with water treatment. | In-situ (1.2 mole % n-butane in air. Contact time - 3 sec.) | 1.2<br>1.2<br>1.2 | 390<br>390<br>390 | 5.0<br>79.0<br>438.0 | 44.5<br>62.5<br>62.2 | 98.2<br>93.6<br>92.4 | 45.3<br>66.7<br>67.0 |
| 8-2 (Comparative) | V/P/O | Organic without HCl and without water treatment. | 400° C. in air for 2 hours. (forced hot air oven) | 1.2<br>1.2<br>1.2<br>1.2 | 400<br>400<br>400<br>400 | 22.5<br>338<br>483<br>507 | 10.5<br>29.2<br>49.2<br>49.7 | 24.0<br>51.2<br>91.0<br>91.2 | 43.6<br>57.1<br>54.0<br>55.1 |

*Contact Time for Ex. 8-1 is 2.5 sec.,
Contact Time for Ex. 8-2 is 3 sec.

EXAMPLE 9

The procedure for catalyst preparation according to Example 1 is followed. After the fresh catalyst material is dried following water treatment, 5% by weight of Sterotex ® (a commercially available stearic and palmitic acid) and 2% by weight of graphite are added. The resulting mixture is pelletized, crushed, and sieved to −10+20 mesh. The catalyst is then activated in situ in a feed stream of 1.2% n-butane in air utilizing the Type 1A reactor at 390° to 400° C. (contact time 2.5 sec.) with a resulting maleic anhydride molar yield after 96 hours of 65.4%.

EXAMPLE 10

The catalyst as prepared in Example 1 is used for the vapor phase oxidation of cis-2-butene. With a feed of 0.8% cis-2-butene in air, the product maleic anhydride molar yield after 130 hours on stream is 52% at 1 sec. contact time and 380° C., again utilizing a Type 1A reactor.

EXAMPLE 11

The catalyst as prepared in Example 1 is used for the vapor phase oxidation of o-xylene. With a feed of 1% o-xylene in air, the product phthalic anhydride molar yield after 2 hours on stream is 54% at 1 sec. contact time and 400° C., again utilizing the Type 1A 5 cc microreactor.

EXAMPLE 12

A fresh catalyst prepared in accordance with Example 1 is shaped into pellets according to the procedure of Example 9 but is not crushed or sieved. These pellets are placed into a Type 2 reactor and activated using a 1.2 mole % n-butane in air stream at a temperature of 400° C. for 40 hours (contact time 2.5 sec.). The reactor temperature is then lowered to 390° C., the contact time is 2.5 sec., and the reaction allowed to proceed for 132 hours (including activation). Product samples are removed at various points during the reaction, analyzed and the results summarized at Table 7.

TABLE 7

| Reactor Temp °C. | Hours on Stream | M.A. Yield % | Butane Conversion % | Selectivity % |
|---|---|---|---|---|
| 400 | 19 | 50.7 | 87.2 | 58.1 |
| 400 | 28 | 51.7 | 89.5 | 57.8 |

TABLE 7-continued

| Reactor Temp °C. | Hours on Stream | M.A. Yield % | Butane Conversion % | Selectivity % |
|---|---|---|---|---|
| 400 | 41 | 57.4 | 94.1 | 61.0 |
| 390 | 57 | 60.4 | 94.1 | 64.2 |
| 390 | 99 | 62.4 | 90.9 | 69.0 |
| 390 | 132 | 62.7 | 94.8 | 66.1 |

From the data of Tables 6 and 7 it can be seen that yields comparable to those obtained by prior art activated catalysts are almost immediately obtained from the fresh catalyst right from the start of the reaction and even before activation is completed. As activation proceeds the yield increases. Thus, since activation conditions include those for running the reaction, the preferred activation procedure does not in reality comprise a separate additional step but merely specifies how long it takes to stabilize yield.

EXAMPLE 13

The following example is intended to illustrate the effect of varying P:V atomic ratios of the starting materials on the yield of the catalyst. Thus, several catalysts are prepared generally in accordance with the procedure of Example 1 with the exception that the amount of $V_2O_5$ and phosphoric acid admixed with isobutanol is varied in a manner sufficient to achieve a ratio of phosphorus to vanadium in these starting materials as described at Table 8. The sized catalysts are placed in a Type 1B reactor (runs 1,3,4) and Type 1A reactor (run 2) and contacted with a stream of n-butane in air. Reactant P:V atomic ratios and those of the fresh catalyst of each run and reaction conditions are summarized in Table 8 together with the yield data associated with each catalyst. As may be seen from the data of Table 8 optimum yield occurs at an initial P:V atomic ratio of reactants of 1.2:1. Note also the similarity in the P:V ratios of the fresh catalysts regardless of the initial P:V atomic ratios of the reactants.

EXAMPLE 14

The first catalyst precursor is prepared and recovered in accordance with the procedure of Example 5 but only a small portion thereof is subjected to the water treatment step in accordance with the procedures as described in Example 1. Activation and use are conducted in accordance with Example 1. After an on stream time of 504 hours, including activation, the product is analyzed for yield and the catalyst is tested by I.R and x-ray diffraction analysis. The results are summarized in Table A.

EXAMPLE 15

The following Example illustrates the preparation of pure B-Phase which is used as a standard in calculating the % B-Phase in the catalysts discussed herein.

To a suspension of $V_2O_5$, 45.7 g (0.25 mole), in 1000 ml of $H_2O$, is slowly added oxalic acid dihydrate, 95 g (0.75 mole), with stirring at 80° C. for 40 min. A clear green solution is obtained. To this solution is added $PO_4H_2NH_4$, 58 g (0.5 mole) under stirring. The color of the solution turns blue and after 1 hour a green precipitate forms in the solution. The reaction is allowed to continue overnight (18 hours) at 80° C., after which the contents of the reaction vessel are cooled and the precipitate filtered. The precipitate is light green and comprises $(NH_4)[(VO)_2C_2O_4(HPO_4)].5H_2O$, a complex salt of vanadyl oxylate bidentate orthophosphate.

The complex, 36 g (0.07 mole), is then calcined in air for 48 hours at 570° C. and then in oxygen for 24 hours at 630° C. to give 14 g of yellow $B-VOPO_4$ (beta oxovanadium phosphate). The $B-VOPO_4$ is then calcined under helium for 4 days at 750° C. to give 4.13 g (0.013 mole) of gray $(VO)_2P_2O_7$.

this accounts for the reduced yield and variation in catalyst properties. The resulting fresh catalyst is tested for P:V atomic ratio and then sized as in Example 1, placed in a Type 1B reactor and the reaction conducted in accordance with the procedure of Example 1. The appropriate activation and reaction conditions are summarized at Table 9. The % B-Phase is determined by x-ray diffraction analysis and the I.R. spectral pattern is determined by mid-infrared spectral analysis. Yield is also determined and the results summarized at Table A.

EXAMPLE 17

The general procedure of Example 5 is followed with the exception that fresh catalyst drying is discontinuous, i.e., the fresh catalyst is dried for 1 hour at 125° C., cooled down overnight and then re-dried at 125° C. for an additional 6 hours. Also, the rate of water evaporation due to atmospheric conditions is reduced even further to 1.23 Lbs/hr. It is believed that the slow evaporation in conjunction with the discontinuous drying can account for the reduced yield associated with this catalyst. The resulting fresh catalyst is sized as in Example 1, placed in a Type 1B reactor and the reaction conducted in accordance with the procedure of Example 1. The appropriate activation and reaction conditions are summarized at Table 9. The catalyst is analyzed as in Example 16 and the results summarized at Table 9 and Table A.

TABLE 8

| Run No. | P:V* | P:V** | Mole % n-butene in Feedstream | Contact Time Sec. | Reaction Temp. °C. | Hours on Stream | M.A. Yield % | Conversion % | Selectivity |
|---|---|---|---|---|---|---|---|---|---|
| 1 | 1.1:1 | 1.02:1 | 1.1 | 2.1 | 400 | 196 | 63.1 | 96.3 | 65.5 |
| 2 | 1.2:1 | 1.03 | 1.2 | 2.5 | 390 | 74.5 | 64.1 | 97.4 | 65.9 |
| 3 | 1.4:1 | 1.11:1 | 1.1 | 2.1 | 407 | 162 | 47.7 | 91.2 | 52.9 |
| 4 | 1.6:1 | 1.12:1 | 1.1 | 4.0 | 386 | 167 | 51.8 | 94.0 | 55.1 |

*initial P:V ratio for starting materials
**actual P:V atomic ratio of fresh catalyst

Comparative Example 6

A dihydrate catalyst precursor is prepared in accordance with the procedures of Harrison U.S. Pat. No. 3,915,892 Col. 5, Lines 34 et seq. The dihydrate precursor is then activated in accordance with pre-treatment method H in a Type 1A reactor. The temperature of the reaction is then lowered to 475° C. and the reaction allowed to proceed to 648 hours using a 1.5 mole % n-butane in air feed stream (contact time 2 sec.). The yield is 35%. This catalyst is then tested by I.R. and x-ray diffraction analysis as described herein to obtain an I.R. spectrum and % B-Phase as well as for P:V atomic ratio. The results are summarized at Table A.

The following Examples 16 to 18 illustrate attempts to prepare catalysts in accordance with the preferred process of the present invention. However, due to various environmental reasons and accident this procedure was unintentionally modified from the preferred preparation procedures. It is believed that as a result of these modifications yield dropped. A description of the changes in catalyst properties which are believed to be associated with these modifications is provided in Section VI herein.

EXAMPLE 16

The general procedure of Example 5 is followed with the exception that due to atmospheric conditions the rate of water evaporation was reduced from 1.53 Lbs/hr in Example 5 to 1.44 Lbs/hr. It is believed that

EXAMPLE 18

The general procedure of Example 5 is followed with the exception that stirrer paddle used to provide agitation broke during overnight refluxing in the first catalyst precursor preparative step. Such breakage occurred after about 12 hours of refluxing. The rate of water evaporated was also only about 1.08 Lbs/hr. The combination of poor agitation and slow evaporation can account for the poor yields associated with this catalyst. The resulting fresh catalyst is sized as in Example 1, placed in a Type 1B reactor and the reaction conducted in accordance with the procedure of Example 1. The appropriate activation and reaction conditions are summarized at Table 9. The catalyst is analyzed as described in Example 16 and the results summarized at Table 9 and Table A.

Comparative Example 7

A catalyst is prepared generally in accordance with Comparative Example 1 with the exception that drying of the first catalyst precursor is conducted at 150° C. until constant weight is achieved, and the fresh catalyst is pelletized and crushed in accordance with the procedures of Example 9. The catalyst is then placed in a Type 1A reactor and subjected to the conditions summarized at Table 9. The product and catalyst are analyzed as in Example 16 and the results summarized at Table A.

TABLE 9

| Ex. or Comp. Ex. No. | Activation | | | | Reaction Conditions | | | | M.A. Yield % | % B-Phase |
|---|---|---|---|---|---|---|---|---|---|---|
| | Mole % n-butane in air-butane feed stream | Contact time sec. | Activation temp. °C. | Hours on Stream | Mole % n-butane in air-butane feed stream | Contact time sec. | Reaction temp. °C. | Hours* on Stream | | |
| Ex. 16 | 1.1 | 2 | 400 | 24 | 1.2 | 2.1 | 384 | 210 | 59 | 5.7 |
| Ex. 17 | 1.2 | 2.1 | 400 | 22 | 1.2 | 2.3 | 390 | 195 | 56.5 | 18.4 |
| Ex. 18 | 1.2 | 2.1 | 401 | 24 | 1.2 | 2.4 | 390 | 315 | 52 | 4.2 |
| C. Ex. 7 | 1.2 | 2.5 | 400 | 24 | 1.2 | 2.5 | 400 | 456 | 52 | 3.3 |

*Includes Activation Time

The principles, preferred embodiments, and modes of operation of the present invention have been described in the foregoing specification. The invention which is intended to be protected herein, however, is not to be construed as limited to the particular forms disclosed, since these are to be regarded as illustrative rather than restrictive. Variations and changes may be made by those skilled in the art without departing from the spirit of the invention.

What is claimed is:

1. A process for oxidizing in the vapor phase at least one feed hydrocarbon to a carboxylic anhydride, said feed hydrocarbon being selected from the group consisting of $C_4$ to $C_{10}$ alkane, $C_4$ to $C_{10}$ alkene, $C_4$ to $C_{14}$ cycloalkane, $C_4$ to $C_{14}$ cycloalkene, alkaryl hydrocarbon wherein the alkyl portion thereof contains from 1 to 10 carbons, and the aryl portion contains from 6 to 14 carbons, and mixtures thereof, which process comprises contacting the feed hydrocarbon, under conditions and in a manner to form at least one carboxylic anhydride, with a catalyst composition comprising vanadium, phosphorus, and oxygen, said catalyst composition prepared by the process which comprises:

(1) reacting in the presence of a liquid organic media, a vanadium containing compound present in said liquid organic media as a heterogeneous suspension, and a phosphorus containing compound, in a manner and under conditions sufficient to form in said liquid organic media a heterogeneous vanadium-phosphorus-oxygen containing first catalyst precursor composition having an atomic ratio of phosphorus to vanadium of from about 0.5:1 to about 2:1, and an average vanadium valence of from about 3.9 to about 4.7;

(2) separating said first catalyst precursor composition from said liquid organic media;

(3) treating said first catalyst precursor composition with at least one part by weight liquid water per part by weight first catalyst precursor composition at a temperature of at least about 30° C. for a period of at least about 0.5 hour to form a second vanadium-phosphorus-oxygen catalyst precursor composition;

(4) separating said second catalyst precursor composition from said water; and (5) activating said second catalyst precursor composition in an atmosphere which excludes the presence of air alone therein.

2. The process of claim 1 wherein the hydrocarbon feed is converted to a carboxylic anhydride selected from the group consisting of maleic anhydride, phthalic anhydride, trimellitic anhydride, pyromellitic anhydride, citraconic anhydride, and mixtures thereof.

3. The process of claim 1 wherein the hydrocarbon feed is selected from the group consisting of n-butane, butene, iso-pentane, orthoxylene, and mixtures thereof.

4. The process of claim 1 wherein said catalyst composition is prepared by the process which comprises:

(1) admixing $V_2O_5$, anhydrous phosphoric acid and isobutanol to form a slurry having $V_2O_5$ suspended therein and phosphoric acid dissolved therein in amounts sufficient to achieve a P:V atomic ratio in said admixture of from about 1:1 to about 1.3:1, (2) refluxing under substantially anhydrous conditions said slurry until the color thereof turns blue to form a heterogeneous first catalyst precursor composition suspended in said slurry having a phosphorus to vanadium atomic ratio of from about 1:1 to about 1.3:1, (3) separating said first catalyst precursor composition from said isobutanol;

(4) treating each part by weight of said first catalyst precursor composition with at least 2 parts by weight water at a temperature of from about 50° to about 150° C. for a period of at least about 1 hour to form a second catalyst precursor composition;

(5) separating said second precursor composition from said water;

(6) activating said second precursor composition in a gaseous mixture comprising air and from about 0.1 to about 1.8 mole %, n-butane, based on the total number of moles of gaseous components in said gaseous mixture.

5. The process of claim 4 wherein Step 4 is conducted by heating said first catalyst precursor in water at a temperature of from about 40° to about 100° C.

6. The process of claim 4 wherein in Step 4 each part by weight of said first catalyst composition is contacted with at least 4 parts by weight water.

7. The process of claim 1 wherein Step 3 of the catalyst preparative procedure is conducted by contacting the first catalyst precursor with a liquid consisting essentially of water.

* * * * *